(12) United States Patent
Margoosian et al.

(10) Patent No.: US 9,481,005 B2
(45) Date of Patent: *Nov. 1, 2016

(54) LIQUID DISPENSING APPLICATOR WITH RADIAL LOCKING SYSTEM

(71) Applicant: Razmik Margoosian, Montreal (CA)

(72) Inventors: Razmik Margoosian, Montreal (CA); Viken Afarian, Montreal (CA)

(73) Assignee: Razmik Margoosian, Montreal (CA)

( * ) Notice: Subject to any disclaimer, the term of this patent is extended or adjusted under 35 U.S.C. 154(b) by 56 days.

This patent is subject to a terminal disclaimer.

(21) Appl. No.: 14/444,376

(22) Filed: Jul. 28, 2014

(65) Prior Publication Data

US 2014/0334865 A1    Nov. 13, 2014

Related U.S. Application Data

(63) Continuation of application No. 13/219,054, filed on Aug. 26, 2011, now Pat. No. 8,899,858.

(51) Int. Cl.
*B43K 5/14* (2006.01)
*B05C 1/06* (2006.01)
*A61F 13/40* (2006.01)
*A61M 35/00* (2006.01)

(52) U.S. Cl.
CPC .............. *B05C 1/06* (2013.01); *A61M 35/003* (2013.01); *A61M 35/006* (2013.01)

(58) Field of Classification Search
CPC .................... A61M 35/006; A61M 35/003

USPC ................................................. 401/132–134
See application file for complete search history.

(56) References Cited

U.S. PATENT DOCUMENTS

| 4,925,327 A * | 5/1990 | Wirt ........................ B65D 47/42 401/132 |
| 6,533,484 B1 * | 3/2003 | Osei ..................... A61M 35/003 222/541.1 |
| 2006/0039742 A1 | 2/2006 | Cable et al. |
| 2010/0168638 A1 * | 7/2010 | Korogi ................ A61M 35/006 604/3 |

* cited by examiner

*Primary Examiner* — Jennifer C Chiang
(74) *Attorney, Agent, or Firm* — SmithAmundsen LLC; Stephen L. Farris; Kelly J. Smith

(57) ABSTRACT

A liquid dispensing applicator can include a container body containing a liquid and having an end with a projection; a head component cooperating with the container body and having a slot for receiving the projection; the container body and the head component being rotatable with respect to each other to enable engagement of the projection and the slot and cause breakage of the projection allowing the liquid to flow from the container body into the head component; and a radial locking system for radially locking the container body and the head component together after rotation with respect to each other. The radial locking system can include a lip-and-channel system where the lip radially slides within the channel and is retained at a far end in a fluid application position.

27 Claims, 20 Drawing Sheets

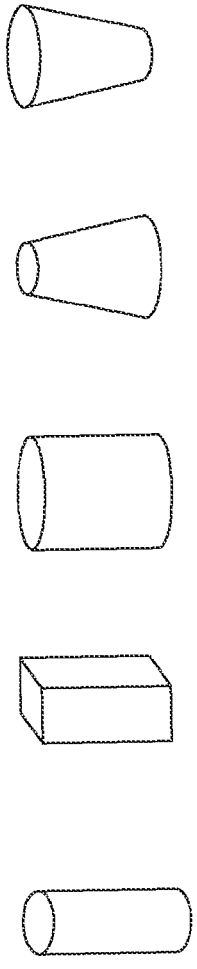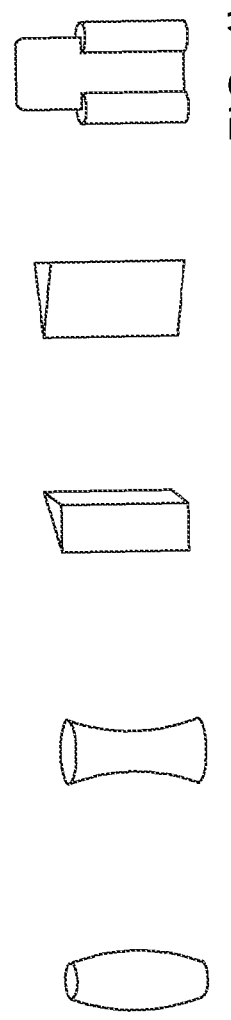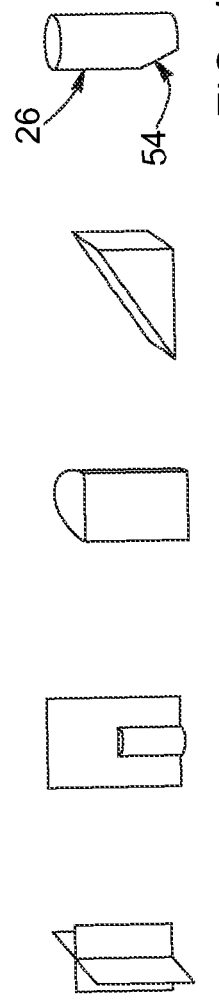

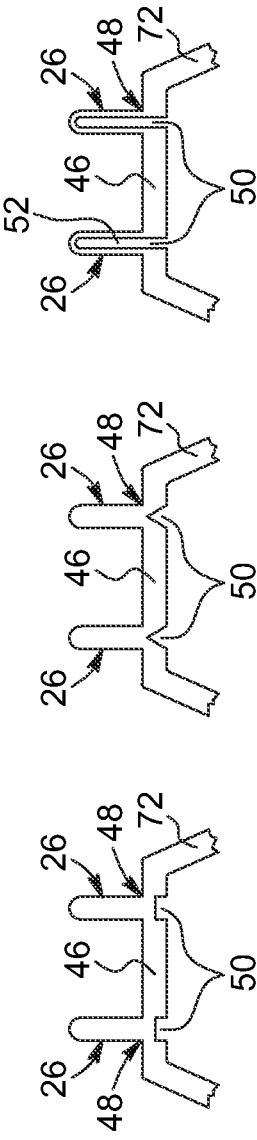

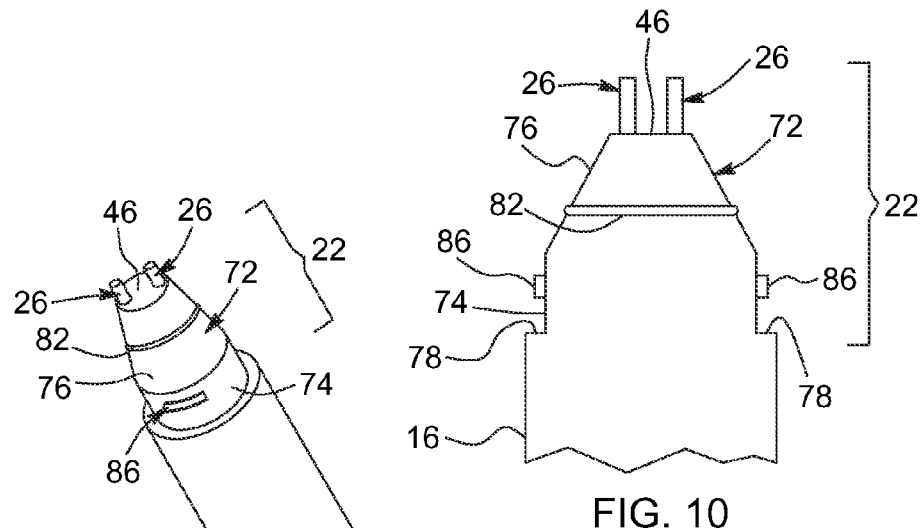
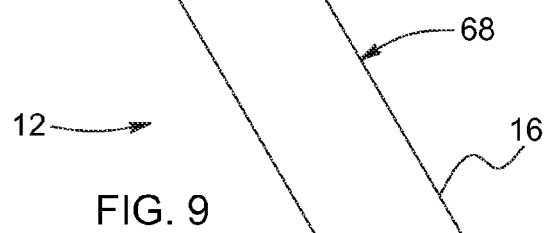
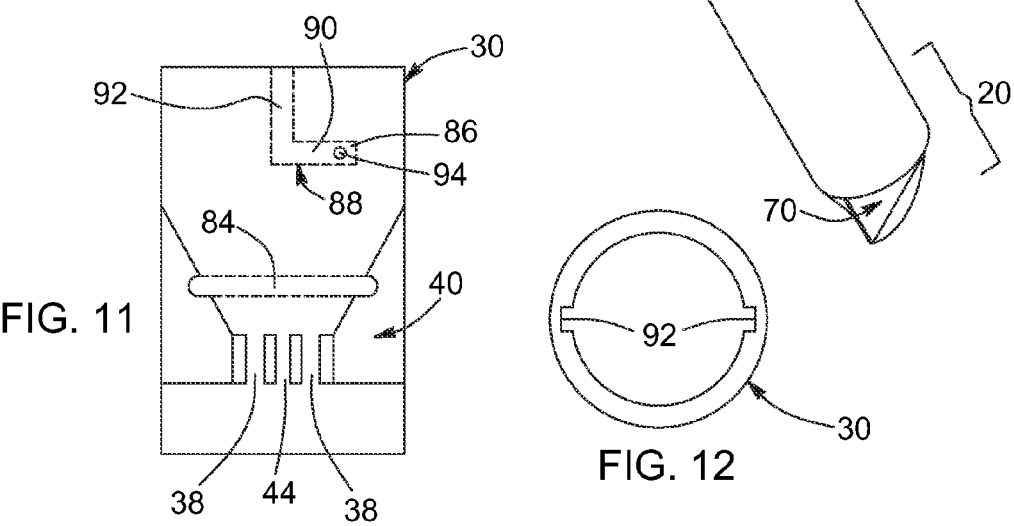
FIG. 9
FIG. 10
FIG. 11
FIG. 12

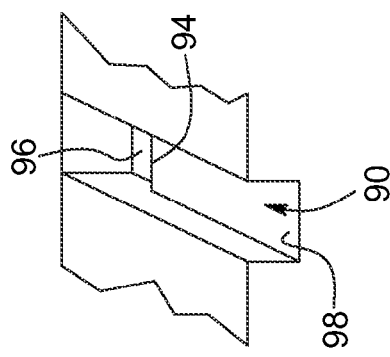
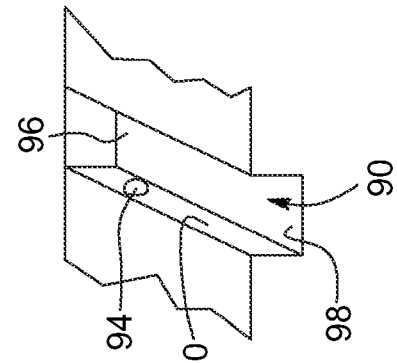
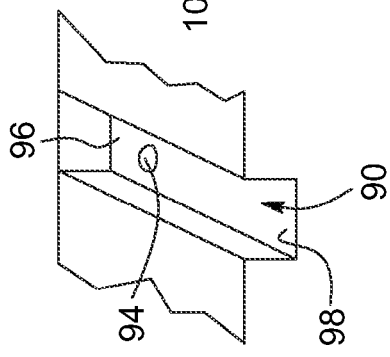
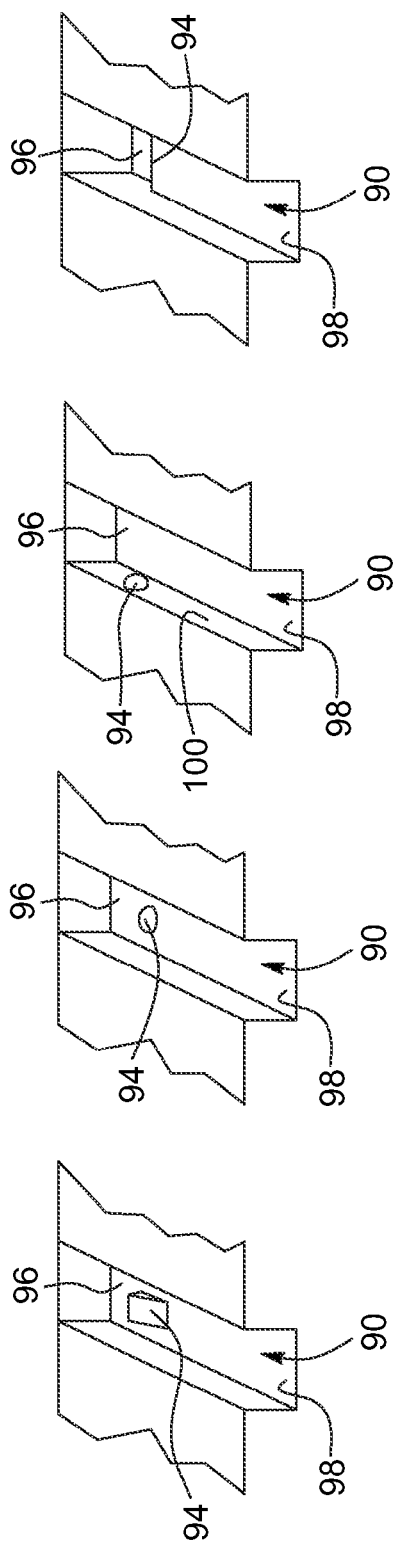
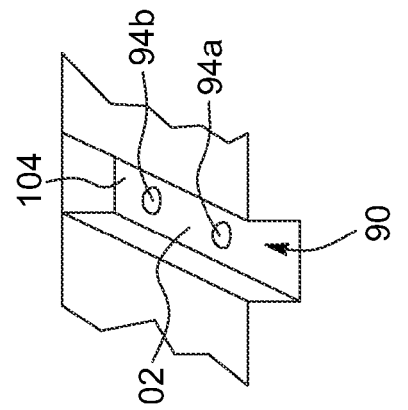
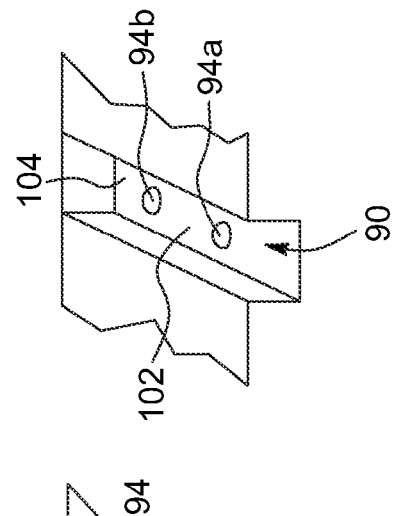
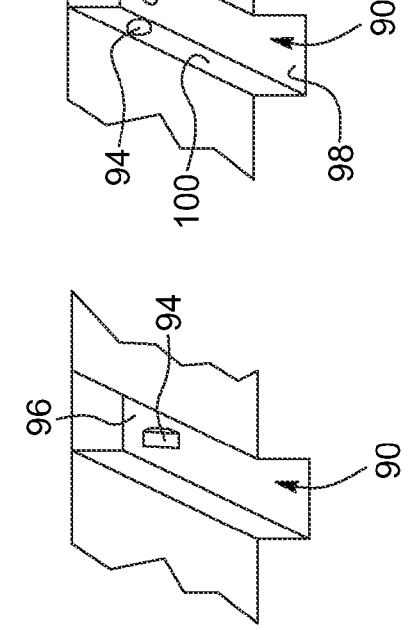

LIQUID DISPENSING APPLICATOR WITH RADIAL LOCKING SYSTEM

CROSS-REFERENCE TO RELATED APPLICATIONS

This application is a continuation of U.S. patent application Ser. No. 13/219,054, filed Aug. 26, 2011.

FIELD OF THE INVENTION

The present invention generally relates to the field of liquid application onto a surface. More particularly, the present invention relates to a liquid dispensing applicator having handle and head components and certain engagement features.

BACKGROUND OF THE INVENTION

Applicators for applying liquids to surfaces are broadly used in several industries such as the medical domain to treat or clean.

Hygiene, reliability, ease of use and safety are some of the desirable characteristics for such applicators.

One way to promote or improve the hygienic characteristics of an applicator may be by ensuring that the applicator can only be used once and then must be thrown away. Another way is by limiting environmental or user access to certain parts of the applicator.

Another consideration for fluid applicators is fluid flow. Fluid flow characteristics are an issue because providing excessive or insufficient amount of liquid on a surface can be detrimental or problematic to the fluid application purpose.

In addition, in particular for medicinal or antiseptic liquids it is desirable to reliably liberate the liquid at the moment of application. For desirable operation, the liquid applicator is often provided with an absorbent material to receive the liquid and then spread the liquid onto a surface. Liberating the liquid into the absorbent material can have several challenges. The absorbent material plays a role in the regulation of the liquid flow and the design of the container component can also affect the fluid flow. In addition, the relative orientation and the position of the different components of the applicator can influence the fluid flow and method of dispensing the liquid.

There are some known liquid applicators that use certain mechanisms to hold, liberate and apply the liquid. One known type of applicator is described in U.S. Pat. No. 7,614,811 B2 (hereafter "Kaufman '811"). Kaufman '811 describes a hand-held dispensing applicator comprising a source of fluid, a frangible applicator tip attached to the fluid source, and an absorbent member attached to the frangible applicator tip. When the frangible applicator tip is broken, fluid flows from the source to the absorbent member, whereby the fluid is applied and spread on a surface. The frangible applicator tip may comprise a support element permanently connected to the fluid source, a relatively rigid tongue element extending outwardly of the support element, and a frangible region there-between. By deflecting the tongue element relative to the support element, the frangible region fractures to thereby permit fluid to flow from the fluid source into the attached absorbent member.

The Kaufman '881 applicator and method of operation have various limitations and disadvantages related to the deflection method and configuration of the tongue element. Having the tongue provide structural support for the absorbent member may also lead to inconsistent performance and complicated manufacture and design requirements.

Another known type of applicator is described in U.S. patent application Ser. No. 11/740,910, published under No. 2007/0286668 (hereafter "Kaufman '910"). Kaufman '910 describes several variants of a hand-held dispensing applicator. One of the variants illustrated in FIGS. 12-26 comprises a container with a tongue element and a stem piece containing a fracture anvil having a cruciform passage for receiving the tongue element when the container and stem piece are coupled together the cruciform passage and the tongue element engage to twist the tongue element at a weakened joinder location resulting in at least partial separation from the container to enable the liquid to flow into the stem piece toward an absorbent material.

Another fluid applicator with tongue-and-slot configuration is described in U.S. Pat. No. 6,533,484 (hereafter "Osei '484"). Osei '484 describes a fluid applicator comprising a solution container having a frangible twist-off member and an applicator head having a receiving member that the twist-off member engages when the applicator head is rotated relative to the solution container to open the container at the twist-off member to enable fluid to flow from the solution container into the applicator head and to an applicating material.

The known fluid applicators have a number of disadvantages related to reliability, ease of use, safety, manufacturing and effective fluid application. There is a need for a liquid dispensing applicator that overcomes at least some of the disadvantages of what is known in this field.

SUMMARY OF THE INVENTION

The present invention responds to the above-mentioned need by providing a liquid dispensing applicator.

In one embodiment of the present invention, there is provided a liquid dispensing applicator comprising: a container body for containing a liquid, the container body having a longitudinal axis about which the container body is rotatable and a first end and a second end, the second end comprising an offset projection located so as to avoid traversing the longitudinal axis; a head component having a passageway having a distal end and a proximal end, the proximal end being for receiving the first end of the container body and the distal end being for applying the liquid onto a surface, the passageway containing a slot system for receiving the offset projection of the container body; wherein the container body and the head component are rotatable with respect to each other to enable engagement of the offset projection and the slot system and cause breakage of the offset projection thereby allowing the liquid to flow from the container body into the passageway of the head component.

In one optional aspect, the offset projection is oriented in parallel relation with respect to the longitudinal axis.

In another optional aspect, the offset projection is spaced away from the longitudinal axis.

In another optional aspect, the offset projection is formed as a solid peg.

In another optional aspect, the offset projection is cylindrical.

In another optional aspect, the offset projection is sized and configured to enable formation of a fluid communication breach in the container body upon breakage of the offset projection, the fluid communication breach having a size allowing liquid flow control. The fluid communication breach may be sized to prevent gravity-induced liquid flow.

In another optional aspect, the fluid communication breach has a diameter of less than about 3 mm. In another optional aspect, the fluid communication breach has a diameter of between about 1.5 mm and about 2 mm.

In another optional aspect, the offset projection is a first offset projection and the container body comprises at least one additional offset projection, constituting a plurality of offset projections.

In another optional aspect, the plurality of offset projections are sized and configured to enable formation of a total fluid communication breach area in the container body upon breakage of the plurality of offset projections, the total fluid communication breach area having a size allowing liquid flow control. In another optional aspect, the total fluid communication breach area is below about 14 mm$^2$. In another optional aspect, the total fluid communication breach area is between about 1.75 mm$^2$ and about 3.15 mm$^2$.

In another optional aspect, the at least one additional offset projection comprises a second offset projection provided in parallel and spaced-apart relation to the first offset projection.

In another optional aspect, the offset projection has a base and a tip and the second end of the container body comprises a weakened region proximate the base of the offset projection. In another optional aspect, the weakened region comprises an indentation in a wall of the second end of the container in opposed relation to the base of the offset projection. In another optional aspect, the indentation is provided with a size and shape conforming to a cross-section of the base of the offset projection.

In another optional aspect, the second end of the container body comprises a frusto-conical wall. In another optional aspect, the passageway of the head component has a cavity with a cooperative shape for receiving and abutting against the frusto-conical wall.

In another optional aspect, the applicator also has an axial coupling system for axially coupling the head component to the container body. In an optional aspect, the axial coupling system comprises a ridge-and-groove system wherein the second end of the container body comprises an annular ridge and the an inner surface of the passageway of the head component comprises an annular groove cooperative with the annular ridge for axially coupling the head component to the container body. The ridge-and-groove system may be snap fitting.

In another optional aspect, the applicator has a radial locking system for radially securing the head component to the container body after rotation thereof and breakage of the offset projection. In an optional aspect, the radial locking system comprises a lip-and-channel system comprising at least one lip and at least one corresponding channel, the lip being radially slidable within the channel, the channel comprising a locking nodule at a far end thereof, wherein rotation from an initial position toward a breakage position causes the lip to slide through the channel and pass over the locking nodule and wherein the locking nodule prevents the lip from sliding back to the initial position. The radial locking system may be configured such that the container body is locked with respect to the head component in a fluid flow position wherein fluid flow apertures of the container body are aligned with openings of the passageway.

In another optional aspect, the container body is formed as a one-piece plastic structure. In another optional aspect, the head component is formed as a one-piece plastic structure.

In another embodiment of the present invention, there is provided a liquid dispensing applicator comprising: a container body for containing a liquid, the container body having a longitudinal axis about which the container body is rotatable and a first end and a second end, the second end comprising a projection; a head component having a passageway having a distal end and a proximal end, the proximal end being for receiving the first end of the container body and the distal end being for applying the liquid onto a surface, the passageway containing a slot system for receiving the projection of the container body; wherein the container body and the head component are rotatable with respect to each other to enable engagement of the projection and the slot system and cause breakage of the projection thereby allowing the liquid to flow from the container body into the passageway of the head component; and a radial locking system for radially locking the container body and the head component together after rotation with respect to each other.

In one optional aspect, the projection is at least one offset projection located so as to avoid traversing the longitudinal axis.

In another optional aspect, the projection is a tongue arranged so as to rotate in response to rotation of the container body with respect to the head component.

In another optional aspect, the radial locking system comprises a lip-and-channel system.

In another optional aspect, the lip-and-channel system comprises at least one lip and at least one corresponding channel with a locking nodule over which the lip passes.

In another optional aspect, the at least one lip is provided on the container body and the at least one corresponding channel is provided on an inner surface of the head component.

In another optional aspect, the at least one lip comprises two opposed lips on either side of the container body and the at least one channel comprises two opposed radial channels.

In another optional aspect, the breakage of the projection forms a fluid communication breach and the radial locking system is configured such that the container body and the head component are locked together so that the fluid communication breach is aligned with the passageway.

In another optional aspect, the first end of the container body has a clamped part and the and the radial locking system is configured such that the container body and the head component are locked together so that the clamped part is oriented for easy and ergonomic grasping.

In another embodiment of the present invention, there is provided a liquid dispensing applicator comprising: a container body for containing a liquid, the container body having a longitudinal axis about which the container body is rotatable and a first end and a second end, the second end comprising a projection; a head component having a passageway having a distal end and a proximal end, the proximal end being for receiving the first end of the container body and the distal end being for applying the liquid onto a surface, the passageway containing a slot system for receiving the projection of the container body; wherein the container body and the head component are rotatable with respect to each other to enable engagement of the projection and the slot system and cause breakage of the projection thereby allowing the liquid to flow from the container body into the passageway of the head component; and a dual-locking system for axially locking the container body and the head component together upon axially coupling and for radially locking the container body and the head component together after rotation with respect to each other.

In one optional aspect, the projection is at least one offset projection located so as to avoid traversing the longitudinal axis.

In another optional aspect, the projection is a tongue arranged so as to rotate in response to rotation of the container body with respect to the head component.

In another optional aspect, the dual-locking system comprises a radial locking system comprising a lip-and-channel system.

In another optional aspect, the lip-and-channel system comprises at least one lip and at least one corresponding radial channel with a locking nodule over which the lip passes for radial locking.

In another optional aspect, the at least one lip is provided on the container body and the at least one corresponding channel is provided on an inner surface of the head component.

In another optional aspect, the at least one lip comprises two opposed lips on either side of the container body and the at least one channel comprises two opposed radial channels.

In another optional aspect, the dual-locking system comprises axial channels communicating with the two radial channels, the axial channels allowing the two lips to be axially inserted therein.

In another optional aspect, the dual-locking system comprises an axial locking system comprising a groove-ridge system.

In another optional aspect, the groove-ridge system comprises the at least one groove provided on the head component and at least one annular ridge provided on the container body for snap-fitting into the corresponding at least one groove.

In another optional aspect, the breakage of the projection forms a fluid communication breach and the radial locking system is configured such that the container body and the head component are locked together so that the fluid communication breach is aligned with the passageway.

In another optional aspect, the first end of the container body has a clamped part and the and the radial locking system is configured such that the container body and the head component are locked together so that the clamped part is oriented for easy and ergonomic grasping.

BRIEF DESCRIPTION OF THE DRAWINGS

FIGS. 4a-4o are perspective view schematics of an offset projection according to embodiments of the present invention.

FIGS. 5a-5g are side cut view schematics of part of an end of a container body according to embodiments of the present invention.

FIG. 9 is a perspective view of a container body with offset projections according to an embodiment of the present invention.

FIG. 10 is a side plan view of an end of the container body according to an embodiment of the present invention.

FIG. 11 is a side cut view of part of a head component according to an embodiment of the present invention.

FIG. 12 is a top plan view of part of a head component according to an embodiment of the present invention.

FIGS. 13a-13f are perspective view schematics of radial locking systems according to embodiments of the present invention.

FIG. 14 is a perspective view schematic of a radial locking system according to an embodiment of the present invention.

DETAILED DESCRIPTION OF PREFERRED EMBODIMENTS

Figure 1:
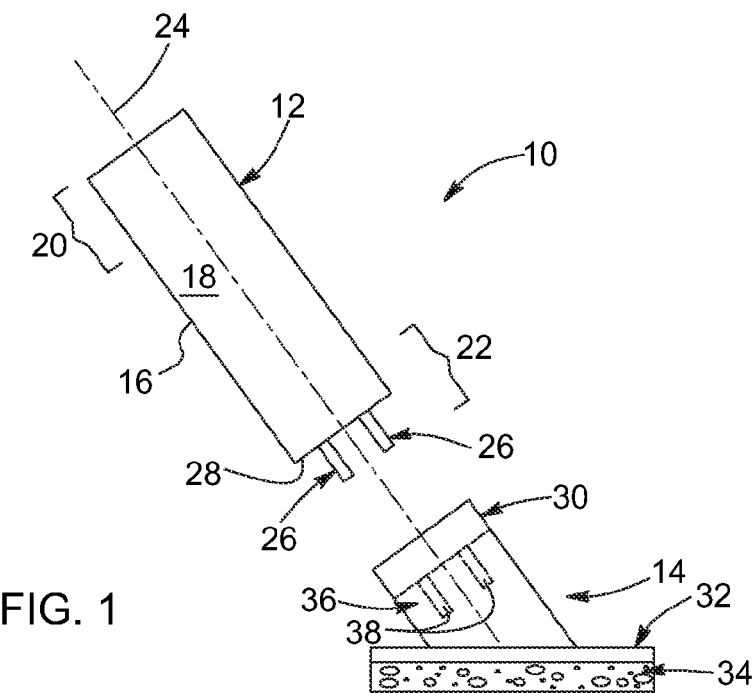
FIG. 1 is a side partial cut, partial exploded and partial transparent view schematic of a liquid dispensing applicator according to an embodiment of the present invention.

Referring to FIG. 1, in a preferred embodiment of the present invention, the liquid dispensing applicator 10 includes two main parts: a container body 12 and a head component 14. These two components may be axially coupled together in operation. Some axial coupling mechanisms that may be used in connection with the present invention will be described further below.

The container body 12 preferably has an outer wall 16 defining a container cavity 18 therein for receiving and holding a liquid. The container body 12 may be a one-piece structure or it may be composed of two or more subcomponents fixed or otherwise coupled together. The container body 12 is preferably formed as a generally elongated tubular structure with opposed first and second ends 20, 22. The container body 12 also has a longitudinal axis 24 about which the container body 12 can rotate. Preferably this longitudinal axis 24 passes through the center line of the tubular structure having a circular cross-section. The container body 12 also has at its second end 22 at least one offset projection 26. The illustrated embodiment of FIG. 1 has a pair of offset projections 26. Each of the offset projections 26 extends from a terminal surface 28 of the container body at the second end 22 thereof. Preferably each offset projection extends at a right angle with respect to the terminal surface 28 and is parallel with respect to the longitudinal axis 24 of the container body 12. When a pair of offset projections 26 is provided, they are preferably equally spaced away from a central point of the second end 22 through which the longitudinal axis 24 passes.

The offset projection is so-called because it is located on the second end of the container body so as to avoid traversing the longitudinal axis. Unlike a central tongue or tab that may span the width of the second end and thus traverse the longitudinal axis 24, the offset projections are located such that each offset projection does not cross the longitudinal axis 24. As will be explained further below, by locating the offset projections in such a way, they are not twisted in response to rotation but are rather deflected and sheared.

Referring still to FIG. 1, the second end 22 of the container body 12 is fit into part of the head component 14. The head component 14 comprises a tubular trunk 30 for receiving the second end 22 of the container body 12 as well as a base portion 32 for supporting an absorbent material 34 such as a sponge. The tubular trunk 30 has a slot system 36 configured for receiving the offset projections 26 of the container body 12.

In operation, the container body 12 is coupled to the head component 14 so as to be axially secured together while allowing rotational movement with respect to each other and so that the offset projections are inserted within the slot system 36. Upon rotation of the container body 12 with respect to the head component 14, the offset projections 26 engage with the slot system 36 causing shearing and breakage at or near to offset projections 26, thereby allowing the liquid to flow from within the container body 12 into and through the head component 14 toward the absorbent material 34. Breakage of the projections 26 results in the formation of apertures in the second end 22 of the container body 12. Such apertures are schematically illustrated and identified with reference character 38 in FIG. 17.

Figure 2:
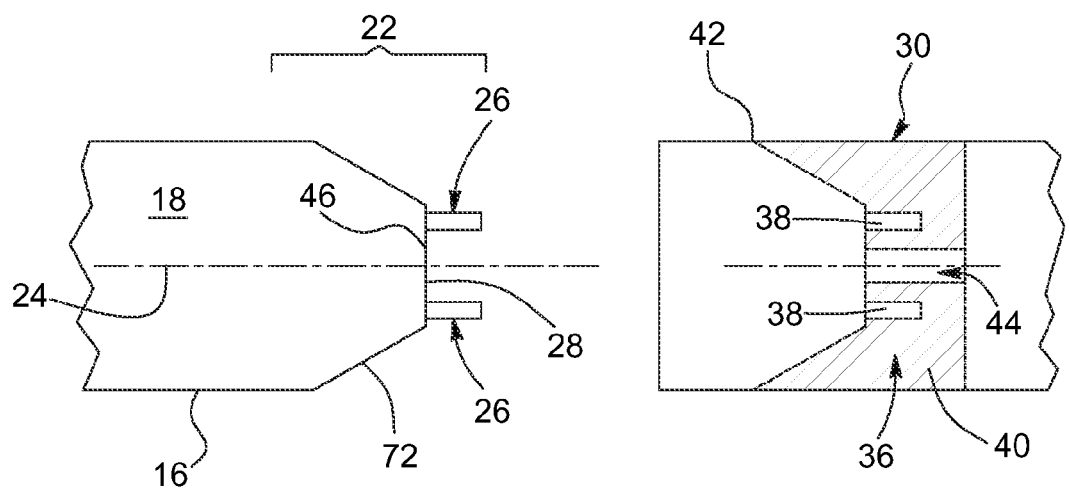
FIG. 2 is a side partial cut, partial exploded and partial transparent view schematic of a part of a liquid dispensing applicator according to an embodiment of the present invention.

Referring now to FIG. 2, the slot system 36 comprises one or more slots 38 sized and configured to receive corresponding ones of the offset projections 26. The slots 38 are formed within the material of the engagement unit 40 which is mounted within or unitary with an outer wall 42 of the tubular trunk 30. In the embodiment illustrated in FIG. 2, the offset projections 26 and the slots 38 have cylindrical shapes and are sized such that the offset projections 26 fit entirely within the slots 38 which each extend partially within the engagement unit 40, rather than extending entirely therethrough. The engagement unit 40 also has a fluid passageway 44, which is sized and configured so as to align with the torn open apertures formed after breakage of the offset projections 26. The fluid passageway 44 is thus in fluid communication with the proximal end of the tubular trunk 30 and allows fluid to flow into the base portion 32 and into the absorbent material 34.

Figure 3D:
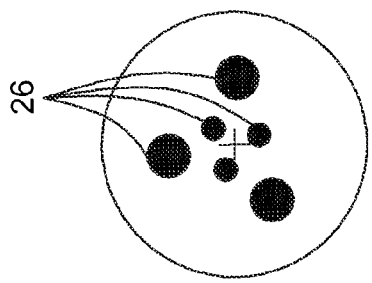
FIGS. 3a-3h are top plan view schematics of part of an end of a container body according to embodiments of the present invention.
Figure 3C:
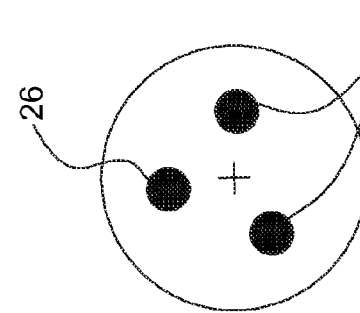
Figure 3B:
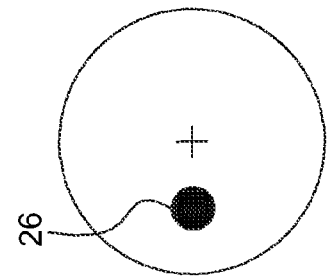
Figure 3A:
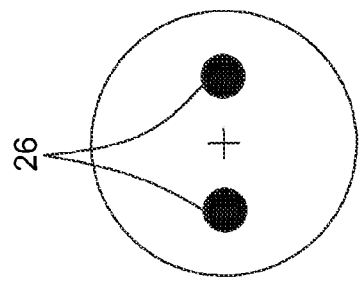
Figure 3H:
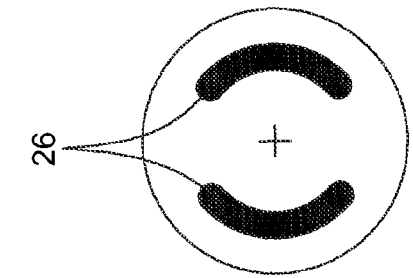
Figure 3G:
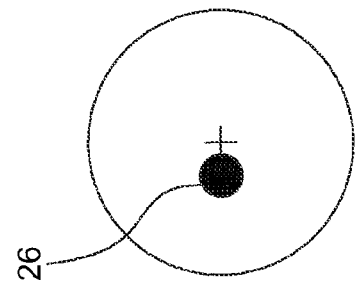
Figure 3F:
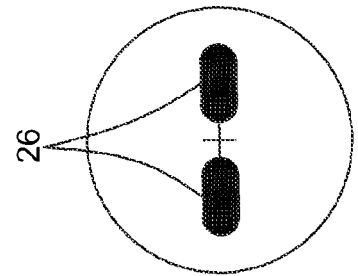

Referring to FIGS. 3a-3g, it should be understood that the at least one offset projection 26 may be provided is several ways and may take various forms. There may be a pair of projections 26 equally spaced away from the axis as shown in FIGS. 3a, 3e, 3f and 3h; multiple projections 26 located around the terminal surface of the container body as shown in FIGS. 3c and 3d; a single projection 26 as shown in FIGS. 3b and 3g; projections that are all spaced away from the central axis as shown in FIGS. 3a-3f and 3h; projections that have a surface aligned with but not traversing the central axis as shown in FIG. 3g; projections that have a circular cross-section as shown in FIGS. 3a-3e and 3g; projections of different sizes on a single container as shown in FIG. 3d; projections that have oval cross-sections as shown in FIG. 3f; and/or projections that have other cross-sections as shown in FIG. 3h. In addition, referring to FIGS. 4a-4o, each offset projection may have various forms, some of which are illustrated here.

It is also noted that the container body is preferably constructed as a unitary one-piece structure made of plastic material. Thus, the projections are preferably unitary with the rest of the container body 12.

Referring to FIGS. 5a-5g, the second end of the container body may have an end wall 46 from which the offset projections 26 extend and which has weakened regions 48 proximate the base of respective offset projections 26. The weakened regions 48 may include indentations 50 as shown in FIGS. 5a-5d and 5g. The weakened regions 48 may also be areas where the end wall 46 is thinner than the rest of the wall of the container body as shown in FIG. 5f. The weakened regions 48 may also include hollow sections 52 of the projections 26 as shown in FIGS. 5c-5e. The hollow sections 52 may be joined with the indentations 50 as shown in FIG. 5c.

Figures 6A, 6B, 6C:
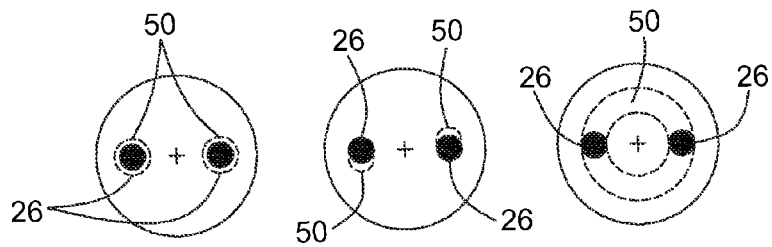
FIGS. 6a-6c are top plan and partial transparent view schematics of part of an end of a container body according to embodiments of the present invention.

Referring to FIGS. 6a-6c, the weakened regions such as indentations 50 may be sized and located in several different ways. The indentations 50 may be provided in a concentric manner with respect to the cross-section of respective offset projections 26 as shown in FIG. 6a; they may be provided offset with respect to the cross-section of respective offset projections 26 as shown in FIG. 6b, for instance offset in the rotational direction in which the projections are sheared and displaced; and they may be provided as an annular continuous indentation 50 encircling the central axis and located below each of the offset projections 26 as shown in FIG. 6c.

Figure 17:
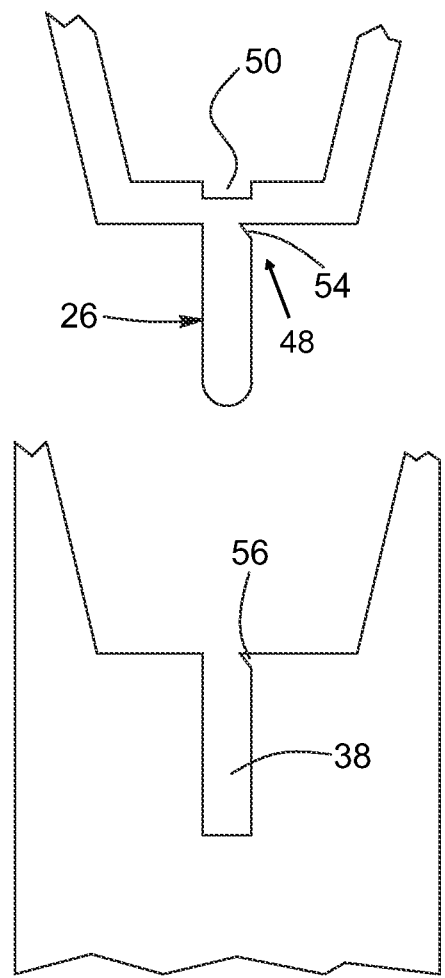
FIG. 17 is a side cut and exploded view schematic of a head component and a container body according to an embodiment of the present invention.

Referring to FIG. 17, the weakened region 48 may also include a notch 54 provided in the base of the offset projection 26 and optionally a corresponding edge 56 in the upper part of the slot 38 for engaging the notch and facilitating breakage of the projection 26.

It should be noted that various other means may be used to facilitate the breaking of the projections and opening up of the apertures in the container body to enable and facilitate fluid flow.

Referring to FIGS. 7a-7m, the engagement unit 40 has one or more slots 38 and one or more fluid passageways 44. In the illustrated embodiments of FIGS. 7a-7l, the preferred rotation of the head component relative to the container body is 90°, thus allowing the torn open apertures of the container body to align with passageways. It should be noted that other configurations are also possible. For instance, FIG. 7m shows a configuration for 180° rotation for ideal alignment.

Figure 3E:
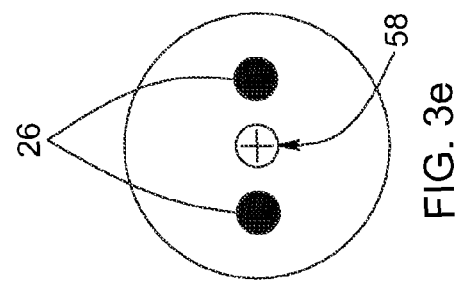
Figures 7A, 7B, 7C, 7D:
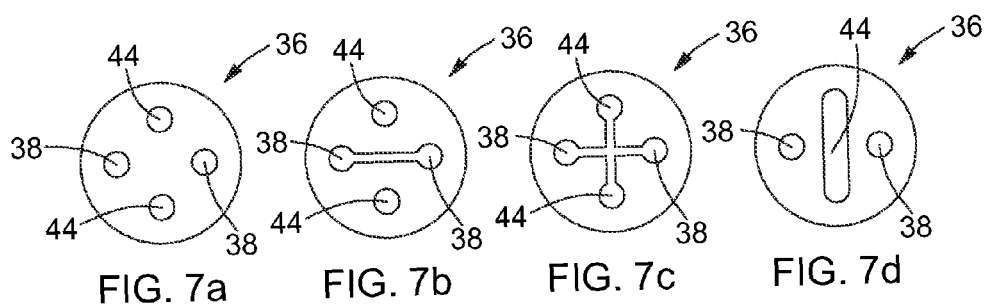
FIGS. 7a-7m are top plan view schematics of part of a slot system of a head component according to embodiments of the present invention.
Figures 7E, 7F, 7G, 7H:
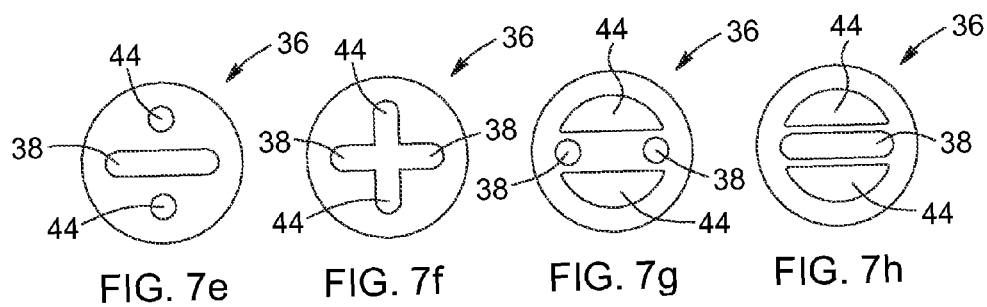
Figures 7I, 7J, 7K, 7L:
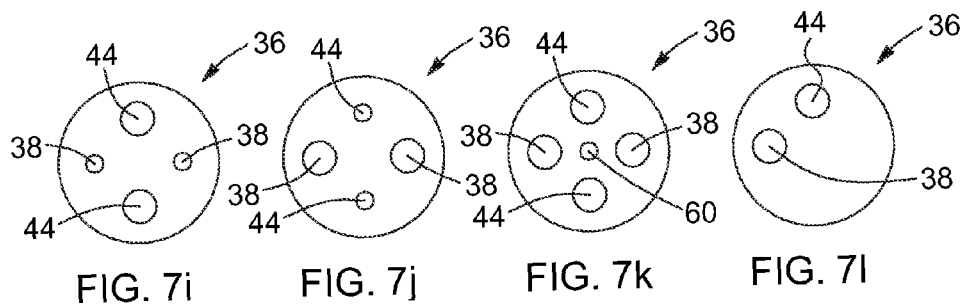
Figure 7M:
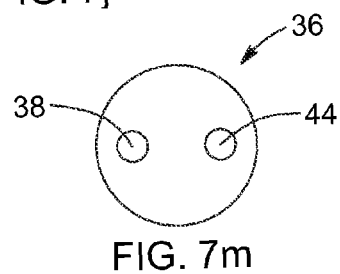

Referring to FIGS. 7k and 3e, the container body may also have a central protuberance 58 aligned with the longitudinal axis and the engagement unit 40 may have a corresponding hole 60 for receiving the central protuberance 58, which does not break but rather helps to stabilise and orient the components together for coupling and rotation.

Figure 8B:
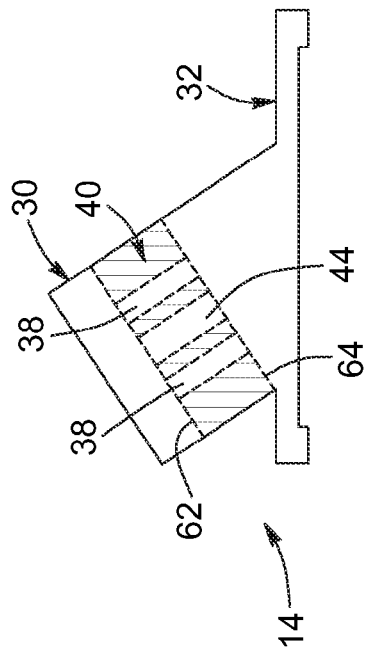
FIGS. 8a-8d are side partial cut and partial transparent view schematics of a head component according to embodiments of the present invention.
Figure 8D:
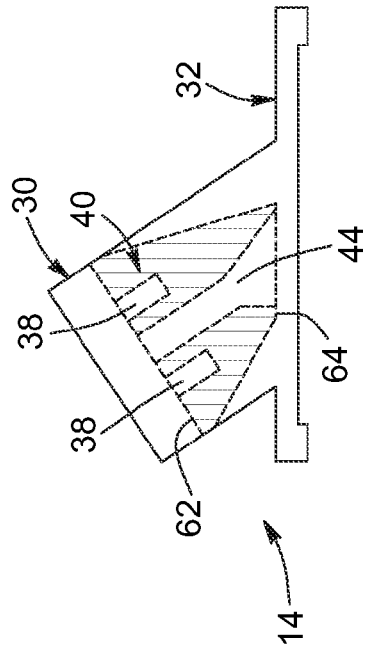
Figure 8A:
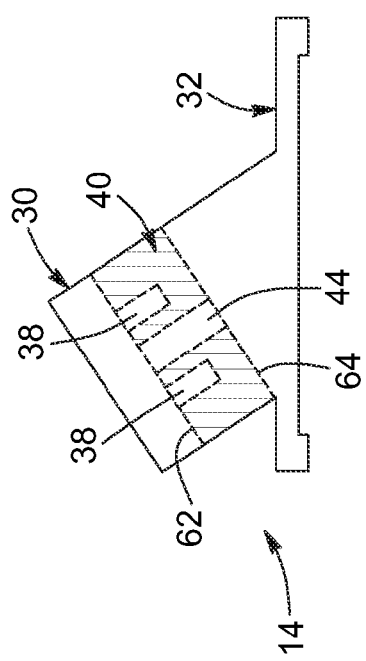
Figure 8C:
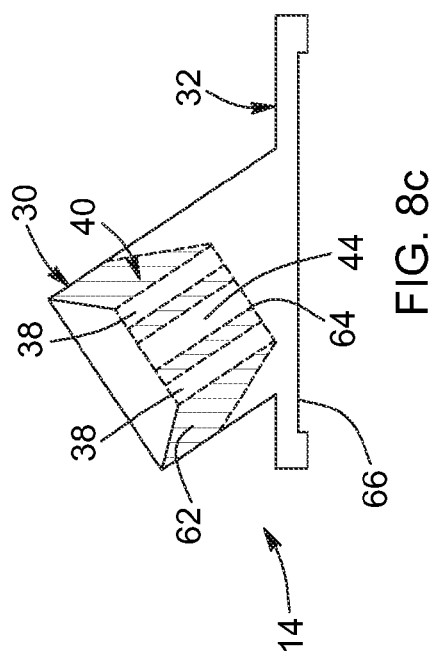

Referring to FIGS. 8a-8d, the fluid passageway 44 and the slots 38 may have several different configurations. For instance, the slots 38 may extend only partially down into the engagement unit material as shown in FIGS. 8a and 8d, or they may extend all the way through as shown in FIGS. 8b and 8c. In addition, the engagement unit 40 may taper inwardly as it extends toward the base portion 32 as shown in FIGS. 8c and 8d. The fluid passageway 44 may have a constant cross-section as shown in FIGS. 8a-8c, or it may have a variable cross-section where at least part of the passageway tapers outwardly as it extends toward the base portion 32 as shown in FIG. 8d. The engagement unit 40 may have a proximal surface 62 and a distal surface 64 which may be parallel to each other as shown in FIGS. 8a-8c, or not. FIG. 8d shows a configuration in which the distal surface 64 is not parallel to the proximal surface 62 but rather to the base portion 32. It should also be noted that the engagement unit 40 may be located at a desired depth with the tubular trunk 30 of the head component 14. In one embodiment, the engagement unit 40 is located relatively deep in the trunk 30 as illustrated in FIG. 8c such that at least part of the distal surface 64 is aligned with the undersurface 66 of a hollow space defined in the base portion for receiving the absorbent material.

Referring now to FIG. 9, the container body 12 is preferably designed to have an elongated tubular structure so as to be manipulated as a handle by a user. The container body 12 has a central portion 68 in between the first end 20 and the second end 22. The central portion 68 is preferably made of a deformable material, such as various plastic materials, so as to be squeezable in order to allow a user to influence the pressure exerted on the liquid and thus control the liquid flow. The first end 20 of the container body 12 is preferably closed by a pinched plastic part 70. Alternatively, the first end 20 may be closed using a variety of other techniques depending on the method of filling the container body 12 with the liquid and on the particular construction and parts used to assemble the container body. In a preferred aspect, the container body 12 is formed as a one-piece structure made from a plastic material. Such a one-piece structure may be manufactured using various moulding techniques, for example. It is also possible to construct the container body is other ways. For example, the container body 12 may be assembled from two or more parts that are fused, melted or screwed together. The first and second ends 20, 22, for example, may be separate components that are permanently or reversibly attached to the central portion 68 to form the container body 12. It should be noted that such attachment between container body subcomponents should be fluid-tight.

Referring still to FIG. 9, the second end 22 of the container body 12 may be configured and provided with several preferred features for advantageous functionality of the liquid dispensing applicator. The second end 22 preferably includes a side wall 72 and the end wall 46. The side wall 72 has a cylindrical section 74 connected to the central portion 68 of the container body 12 and has a frusto-conical section 76 extending between and connecting the cylindrical section 74 and the end wall 46. The cylindrical section 74 has a smaller diameter than that of the central portion 68, preferably sized such that the entire second end 22 of the container body can be inserted within the tubular trunk of the head component. An annular ledge 78 defined between the cylindrical section 72 and the central portion 68 can abut on a corresponding annular surface (identified with reference character 80 in FIG. 15) of the head component. The surface of the outer wall 16 of the container body thus aligns to be generally coplanar with the outer surface of the tubular trunk, thereby providing a flush surface for the assembled applicator. The side wall 72 is preferably provided as a rigid, thick or strengthened plastic wall compared to the outer wall 16 of the rest of the container body, especially compared to that of the central portion 68.

In another preferred embodiment, the liquid dispensing applicator has a double-locking mechanism for both axially and radially locking the head component to the container body in the desired functional positions.

Preferably the axial locking system comprises ridge-and-groove system wherein one of the components has a ridge and the other component has a groove for receiving the ridge when the components are axially coupled together. Preferably the ridge-and-groove system is snap fitting. It is also noted that there may be multiple ridges and corresponding grooves for providing multiple snap fit connection points.

Referring to FIG. 9, the second end 22 of the container body 12, preferably the frusto-conical section 72 comprises the annular ridge 82. Referring to FIG. 11 an inner surface of the tubular trunk 30 has the annular groove 84 that is cooperative with the annular ridge for axially coupling the head component to the container body. It should be noted that the annular ridge may alternatively be provided on the head component and the annular groove may be provided on the second end of the container body.

Preferably the radial locking system for radially securing the head component to the container body after rotation thereof and breakage of the offset projection comprises a lip-and-channel system wherein one of the components has at least one lip and the other component has at least one corresponding channel with a locking nodule.

Referring to FIG. 10, the second end 22 of the container body 12, preferably the cylindrical section 74, comprises the lip 86. Preferably there are two opposed lips 86 one on each side of the container body 12. Referring to FIG. 11, an inner surface of the tubular trunk 30 has the channel 88. The channel 88 preferably has a radial channel section 90 and an axial channel section 92, which are interconnected so that the lip can slide axially through the axial channel 92 when axially coupling the two head component to the container body and then the lip can slide radially along the radial channel 90 when the components are rotated with respect to each other. The lip 86 is radially slidable within the radial channel section 90, which has a locking nodule 94 at its far end 96. When releasing the liquid from the container body 12, rotation from an initial position toward a breakage and liquid release position causes the lip 86 to slide through the radial channel 90 and pass over the locking nodule 94 and the locking nodule 94 then prevents the lip 86 from sliding back. The far end 96 of the radial channel 90 is sized and configured to receive the lip 86. It should be noted that the lips may alternatively be provided on the head component and the channels may be provided on the second end of the container body. Having two opposed lips and two opposed corresponding channels enables, for example, improved guiding and stability for rotating and radial locking.

Referring to FIG. 12, there are preferably two opposed channels such that the axial channel sections 92 are on either side of the tubular trunk 30.

Referring to FIGS. 13a-13f, the locking nodule 94 can be provided in a number of ways within the radial channel 90. The locking nodule 94 can take the form of a round bump as shown in FIGS. 13b and 13c, an inclined block with a straight back edge as shown in FIG. 13a, a ledge defined by a sloping radial channel as shown in FIG. 13d, or another shape or form. The locking nodule 94 may also be provided on a bottom surface 96 or a side surface 100 of the radial channel 90. FIG. 13e shows a flexible tab-like nodule and FIG. 13f shows a configuration using two nodules on the bottom and side surfaces of the radial channel 90.

In addition, the radial locking system may be configured to have multiple or staged locking positions.

Referring to FIG. 14, the radial channel 90 may have multiple locking nodules including a first nodule 94a and a second nodule 94b. Rotation of the head component relative to the container body will cause the lip to pass over the first nodule 94 and retaining the lip in a first channel section 102 and securing the components together at an intermediate position. Further rotation of the components causes the lip to pass over the second nodule 94b and to be retained in the second channel section 104 at the end of the radial channel 90. It should be noted that the passageway and offset projections may be configure and oriented such that in the intermediate rotational position, the liquid can be release in a different manner compared to a full rotation position, e.g. different passageway diameters could enable different flow control and flow rate of liquid. In one aspect, the fluid communication breaches formed by breakage of the projections are sized to prevent gravity-induced liquid flow, thus allowing fluid to be retained within the container body unless the user exerts pressure on the container body.

With regard to the radial locking system, various different structures and interworking parts may be provided to allow the head component to be secured to the container body after rotation. For instance, instead of having a channel inset into the inner surface of the tubular trunk of the head component, there may be an elongated slot through the tubular trunk and the container body may have a rod projecting so as to pass through the elongate slot and be slidable therein. The elongated slot may have a nodule, edge or another structural element at its far end to resist back sliding of the rod after rotation.

Figure 15:
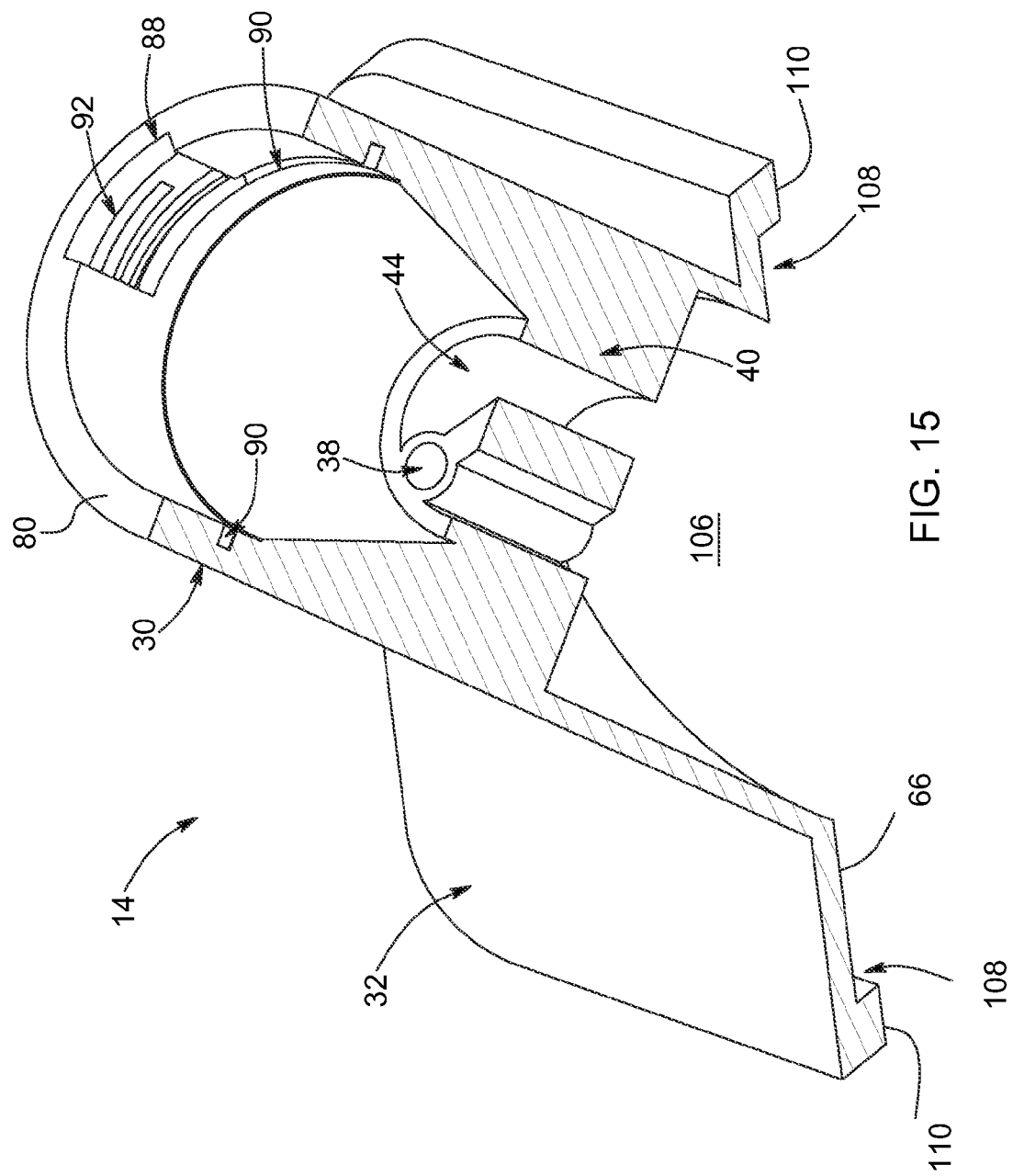
FIG. 15 is a top perspective cross-sectional view of part of the head component according to an embodiment of the present invention.
Figure 16:
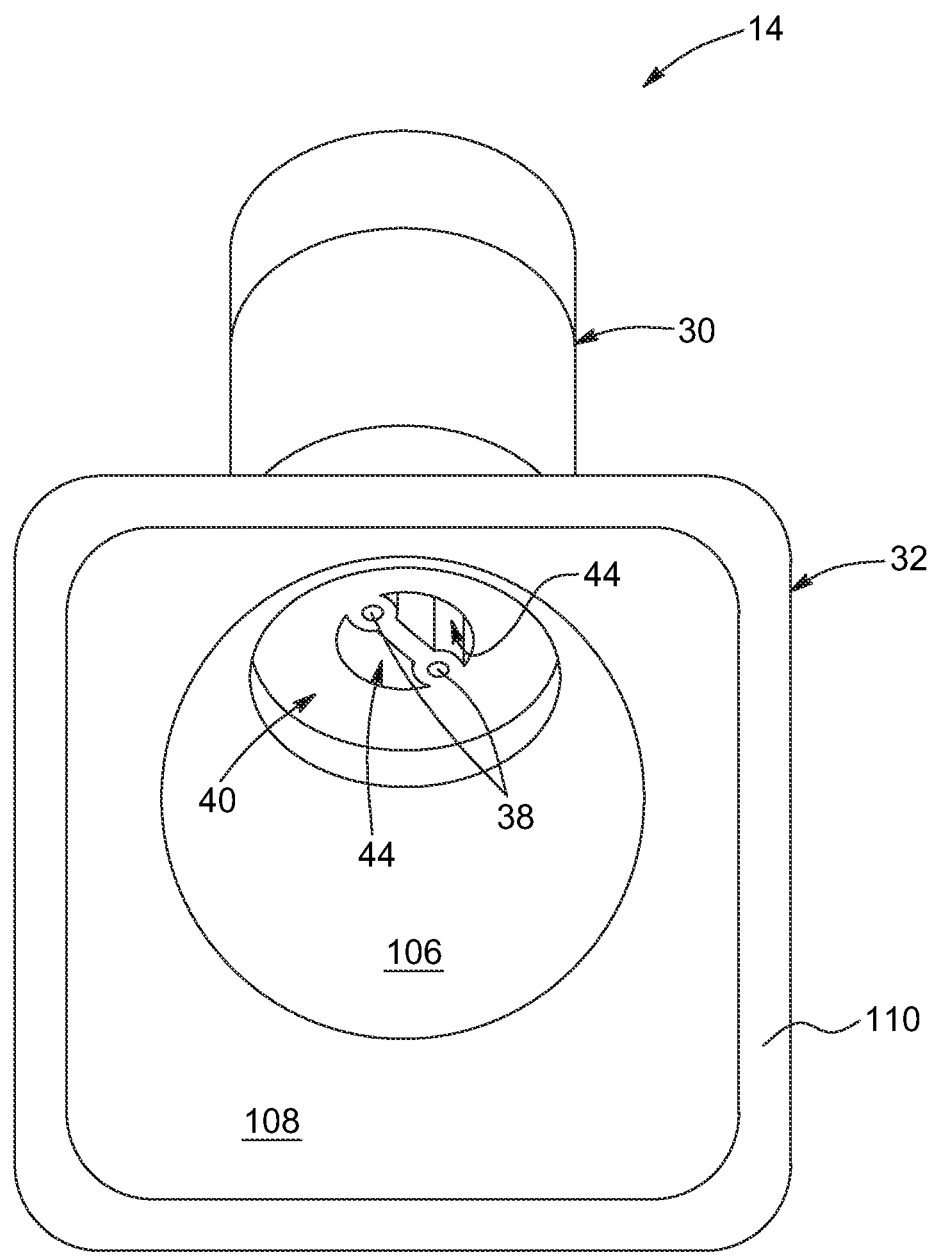
FIG. 16 is a bottom perspective view of the head component according to an embodiment of the present invention.

Referring to FIG. 15, once the offset projections have been sheared and liquid has been released though the passageway 44, the fluid flows through a downstream cavity 106 and into the base portion 32 of the head component 14. The base portion 32 has an inset region 108 which has the bottom surface 66. The base portion 32 also has a lower perimeter 110 surrounding the inset region 108. Preferably the absorbent material is attached to the lower perimeter 110 leaving a space between the absorbent material and the bottom surface 66. This spacing is preferably sized and provided so as to allow the liquid to flow into that inset region 108 to improve even distribution over the absorbent material (not illustrated here). The absorbent material is mounted to the base portion preferably around the perimeter 110 using an adhesive. Once the liquid penetrates through the absorbent material it can be dispensed by the absorbent material onto the desired surface.

Each offset projection may have a proximal side and distal side with respect to the center of the end tip. The proximal side may have a surface preferably located in spaced relation from the central axis by a distance. The distal side of the offset projection may preferably have a surface located so as to be near or defining a smooth line with the surface of the frusto-conical section of the end tip. While the location and configuration of the offset projections may be varied, it may be preferable that each offset projection is located closer to the perimeter of the end of the container body than to the longitudinal axis. Location of the offset projections should also be coordinated with their size, shape and configuration to ensure adequate breakage of the projections in response to rotation of the container body relative to the head component and to facilitate manufacturing and handling of the liquid dispensing applicator. For instance, projections located further away from the longitudinal axis may be preferred for breaking in response to rotation.

Each of the projections also has a top end and bottom end, which may have the same or different cross-section and shape.

Figure 27:
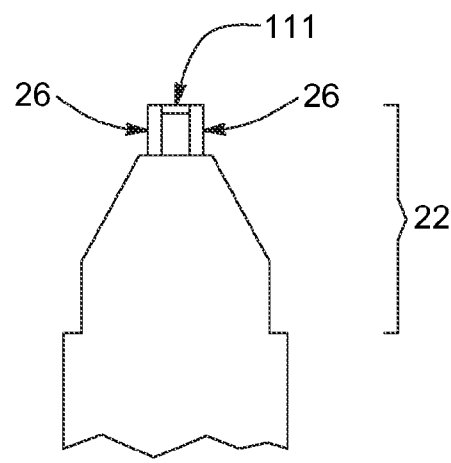
FIG. 27 is a side plan view schematic of an end of the container body according to another embodiment of the present invention.
Figure 28A:
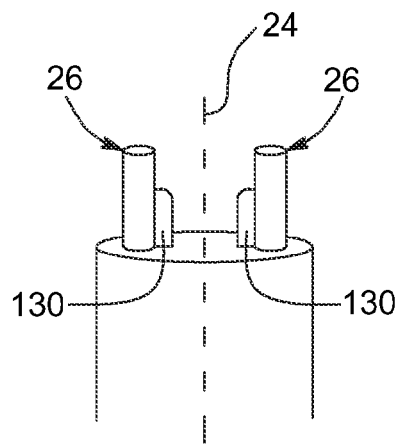
FIGS. 28a-28d are side perspective view schematics of configurations of offset projections with support tabs.
Figure 28B:
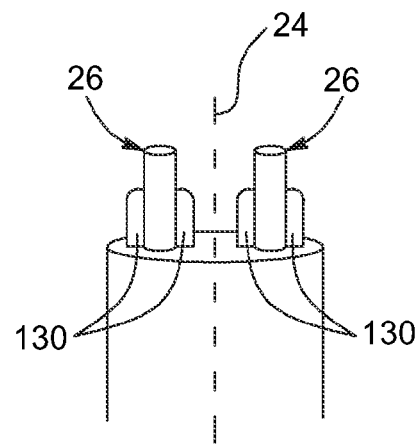
Figure 28C:
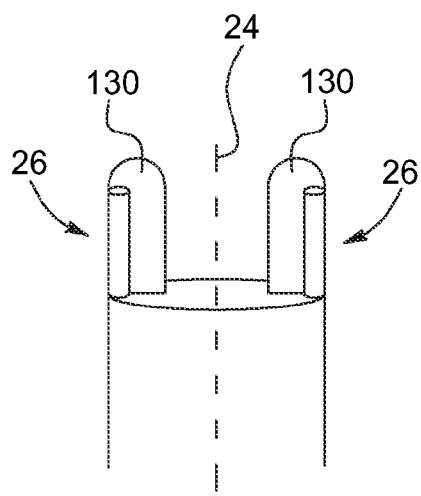
Figure 28D:
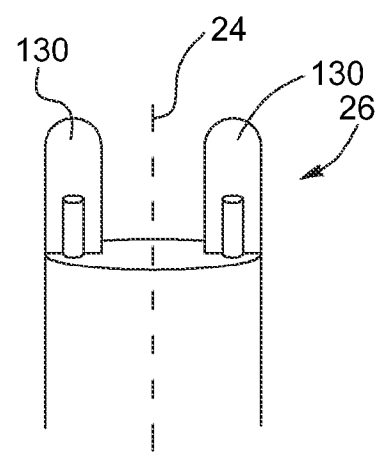

Referring now to FIG. 27, when there are multiple offset projections 26 may be joined together via a bridging member 111. There may be one or more bridging members 111 which may be arranged in between the offset projections 26 for stabilizing the projections during manufacturing, handling and packaging of the liquid dispensing applicator. For instance, when the liquid dispensing applicator comprises one-piece moulded container body and one-piece moulded head component, there may be a bridging member 111 that is also unitary with the offset projections 26 for stabilizing them. The bridging member 111 may be structured and configured such that upon insertion of the container body into the head component, the bridging member folds, moves or fractures to allow the offset projections to be received within the slot system. The bridging member 111 may be provided between the far ends of the offset projections, in the middle or in another location and may have a variety of forms and structures.

Figures 18, 19:
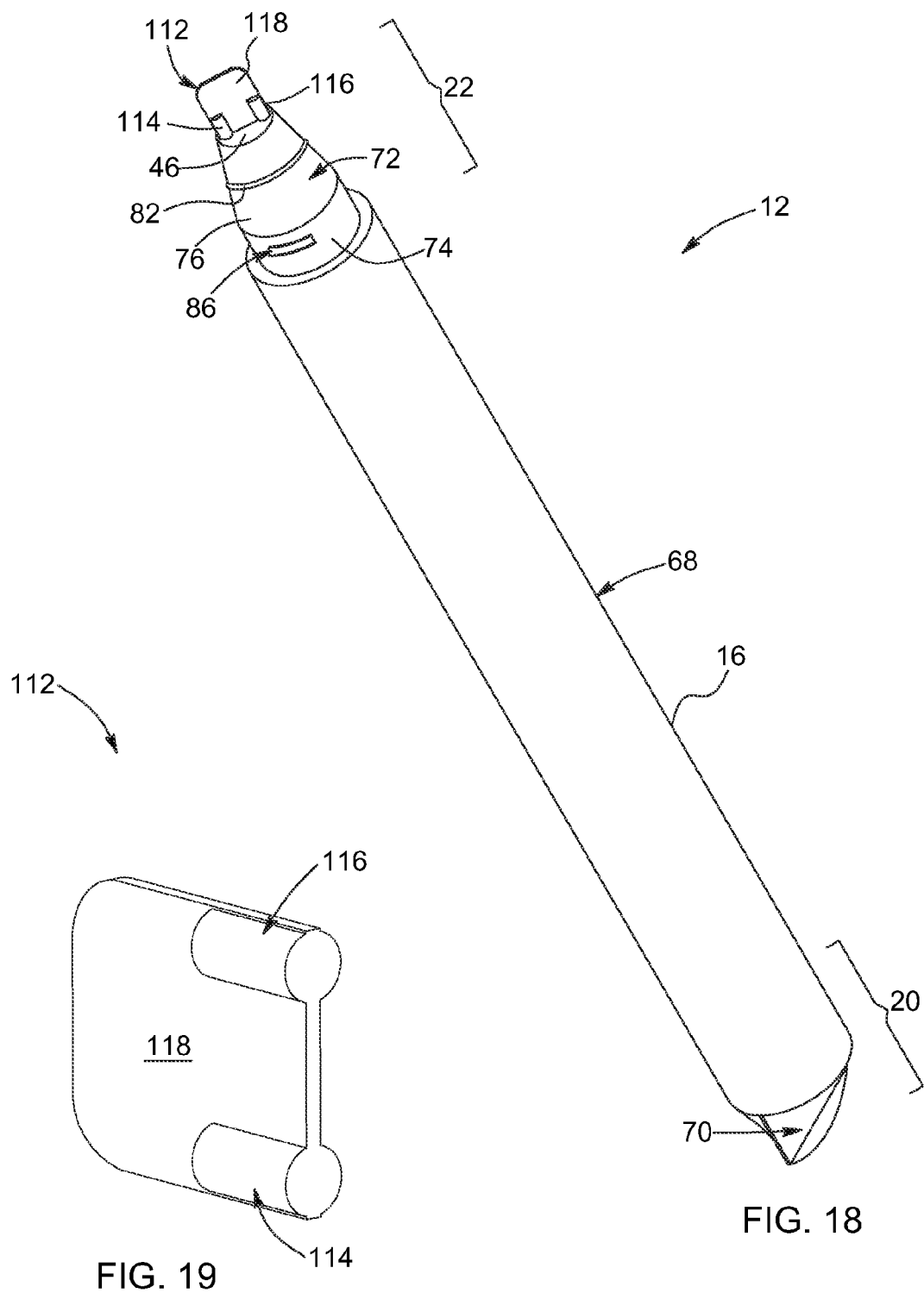
FIG. 18 is a perspective view of a container body with tongue according to an embodiment of the present invention.
FIG. 19 is an isolated perspective view of a tongue of the container body according to an embodiment of the present invention.

According to another embodiment of the present invention, referring to FIG. 18, the container body 12 has at its second end 22 a tongue 112 that extends forwardly from the end surface 46. The tongue 112 also preferably includes two ribs 114, 116 which are provided at the opposed edged and at the base of a tab-shaped portion 118. The tongue has breakable regions that are connected to the tip of the second end 22 as will be explained further below in relation to the operation of the container body and head components when releasing the liquid.

It should be noted that this embodiment has many similar features as the embodiment described above, especially in relation to the axial and radial locking systems as well as the configuration and shape of the second end 22 of the container body 12. In addition, most head component constructions can be used with either embodiment of the container body 12 corresponding to FIG. 9 or FIG. 18.

In operation, the container body 12 is coupled with the head component 14 and the tongue 112 engages part of the head component 14 such that rotation of the container body 12 relative to the head component 14 causes the tongue 112 to twist and break away and create fluid communication between the container body 12 and the interior of head component 14.

Figure 20:
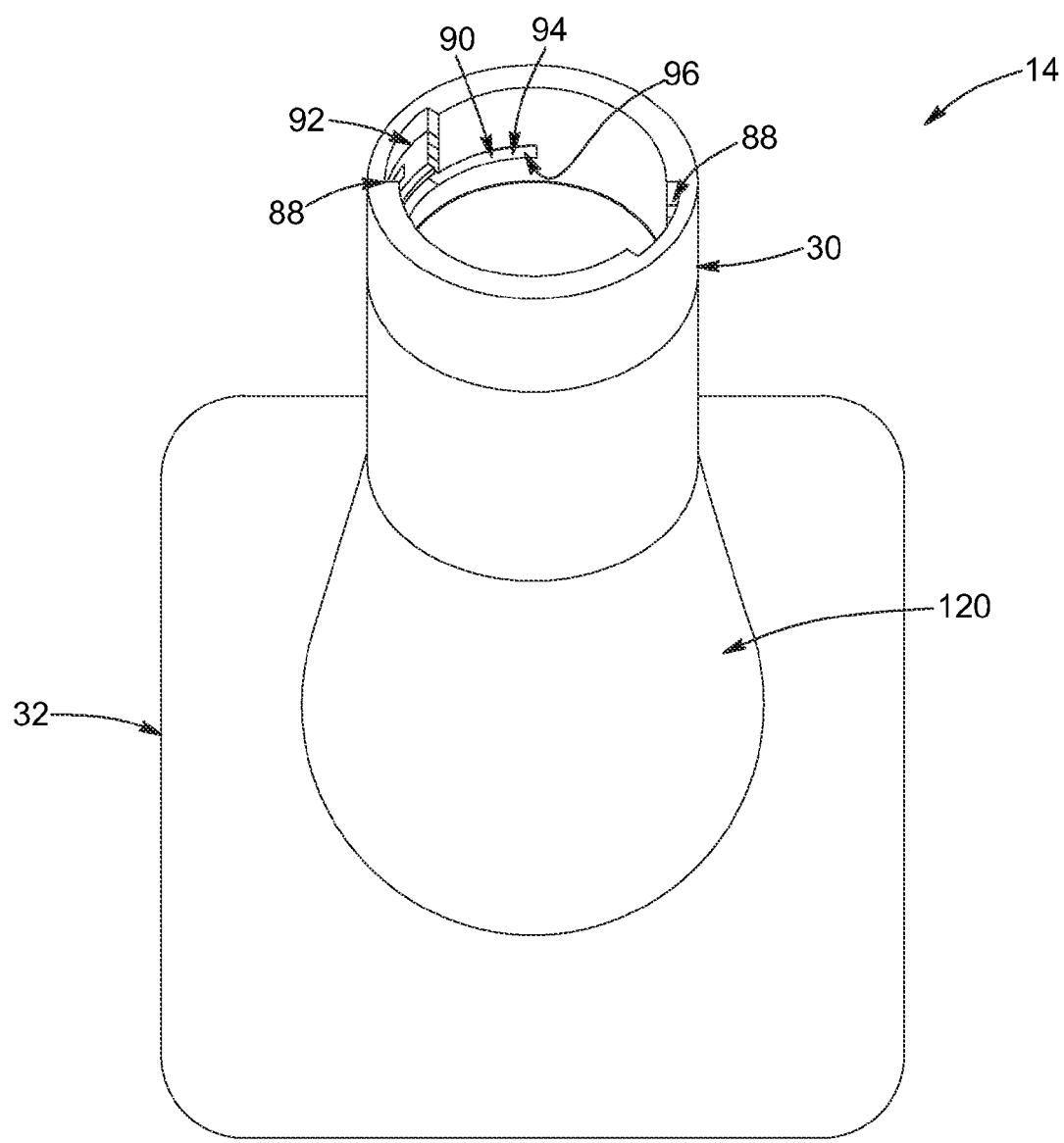
FIG. 20 is a perspective view of the head component according to an embodiment of the present invention.
Figure 21:
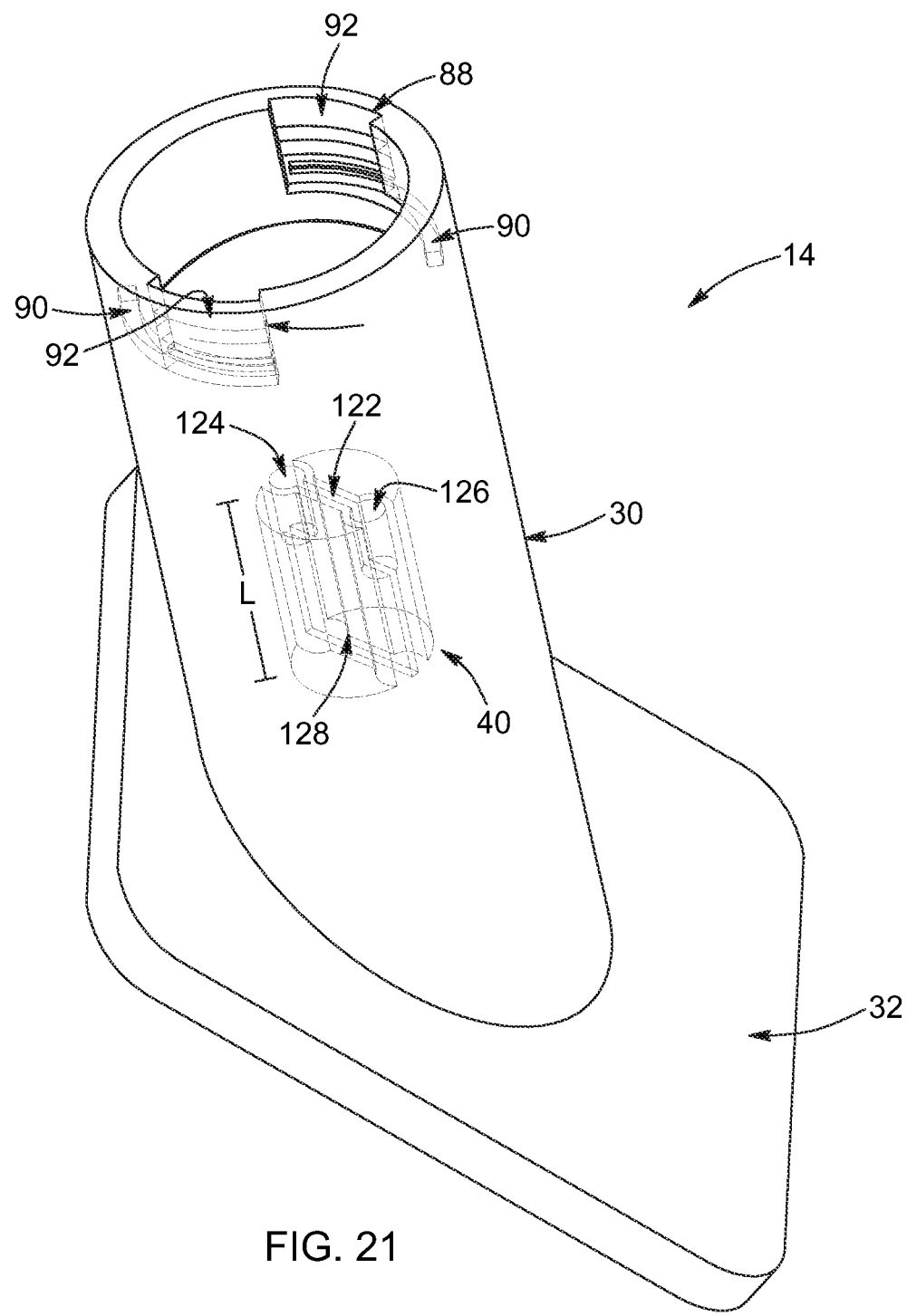
FIG. 21 is a partially transparent perspective view of the head component according to an embodiment of the present invention, wherein engagement unit, recesses and grooves are shown transparently in dotted lines.
Figure 22:
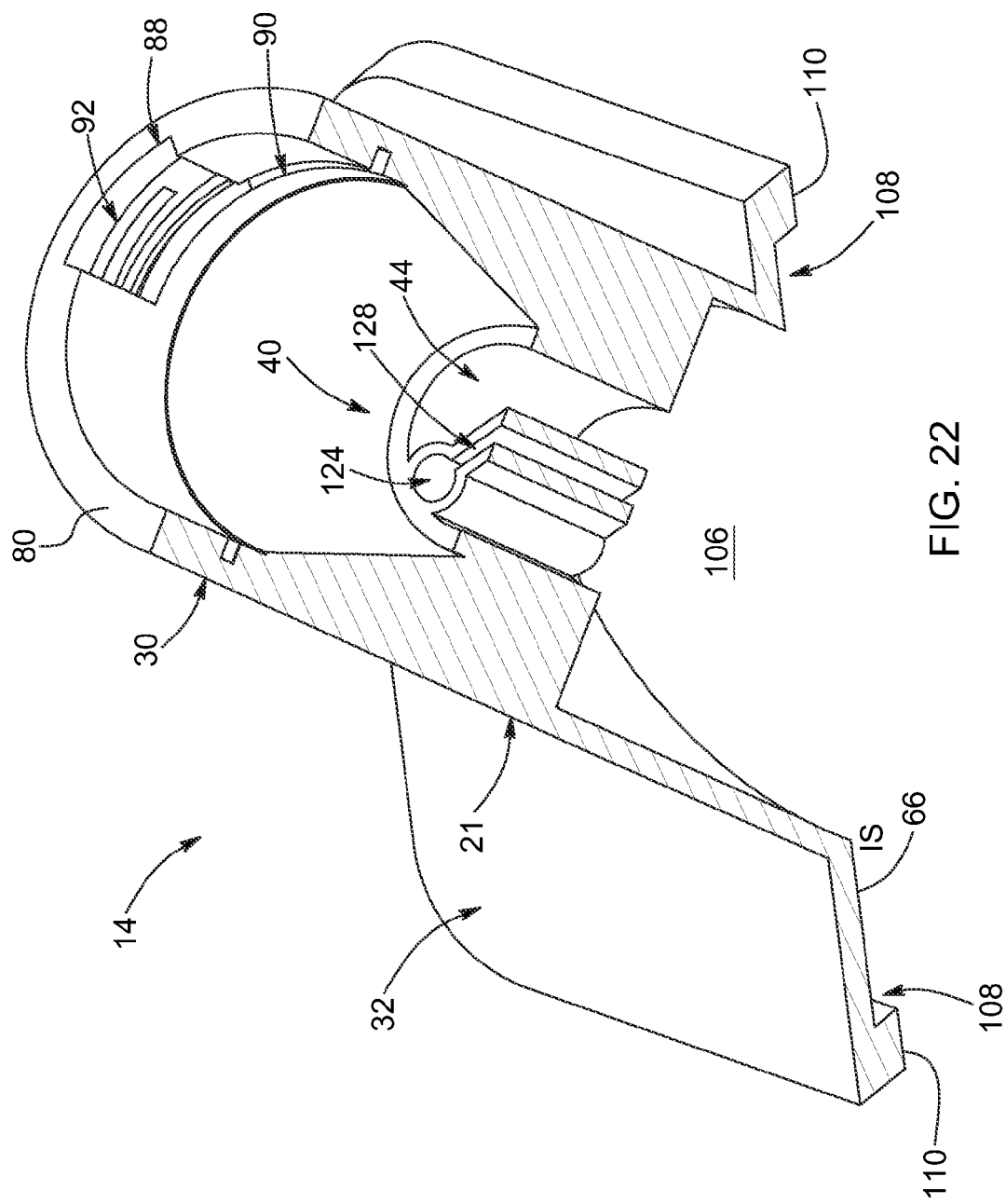
FIG. 22 is a perspective cross-sectional view of the structure of the head component according to an embodiment of the present invention.
Figure 23:
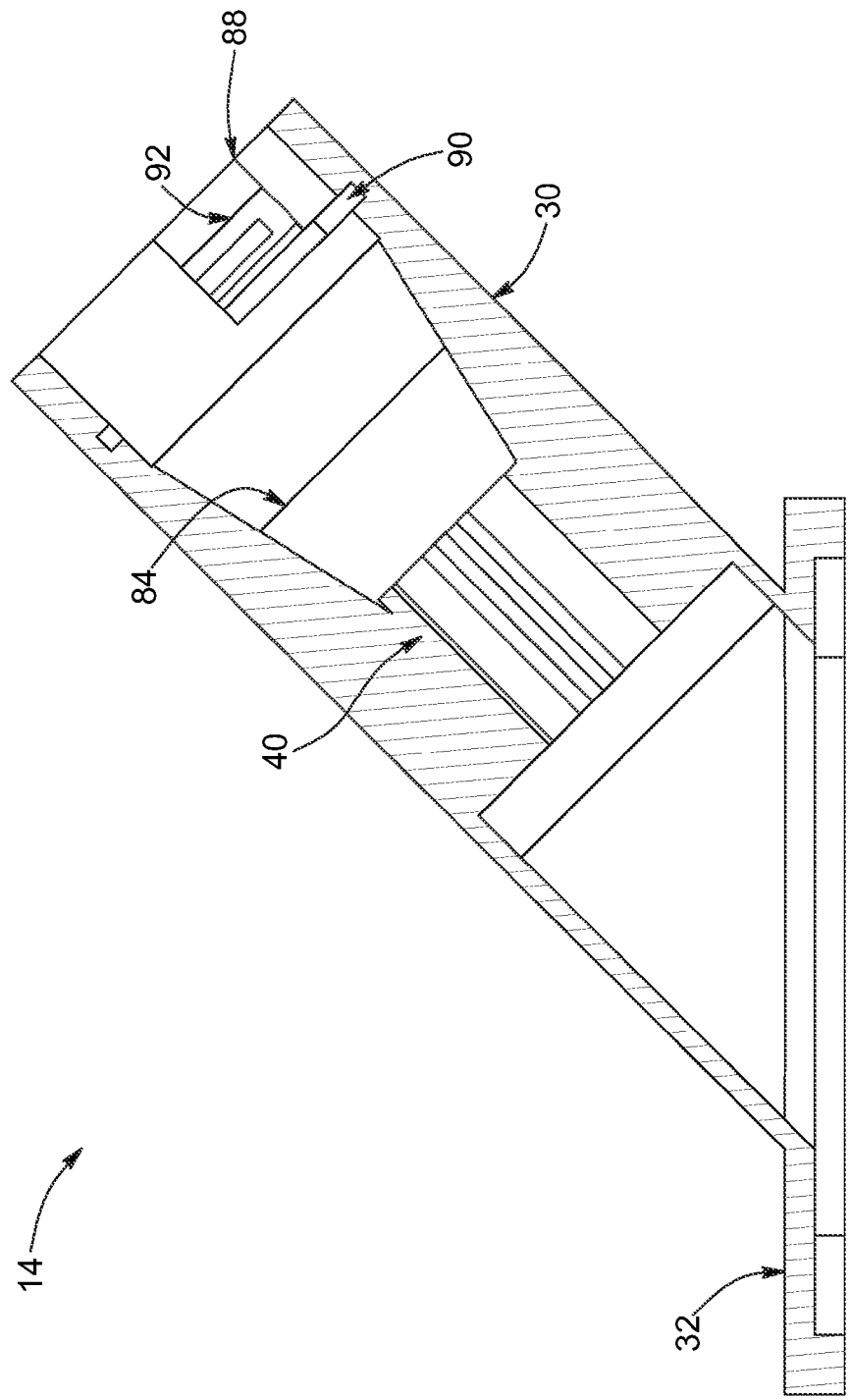
FIG. 23 is a cross-sectional side view of the head component.
Figure 24:
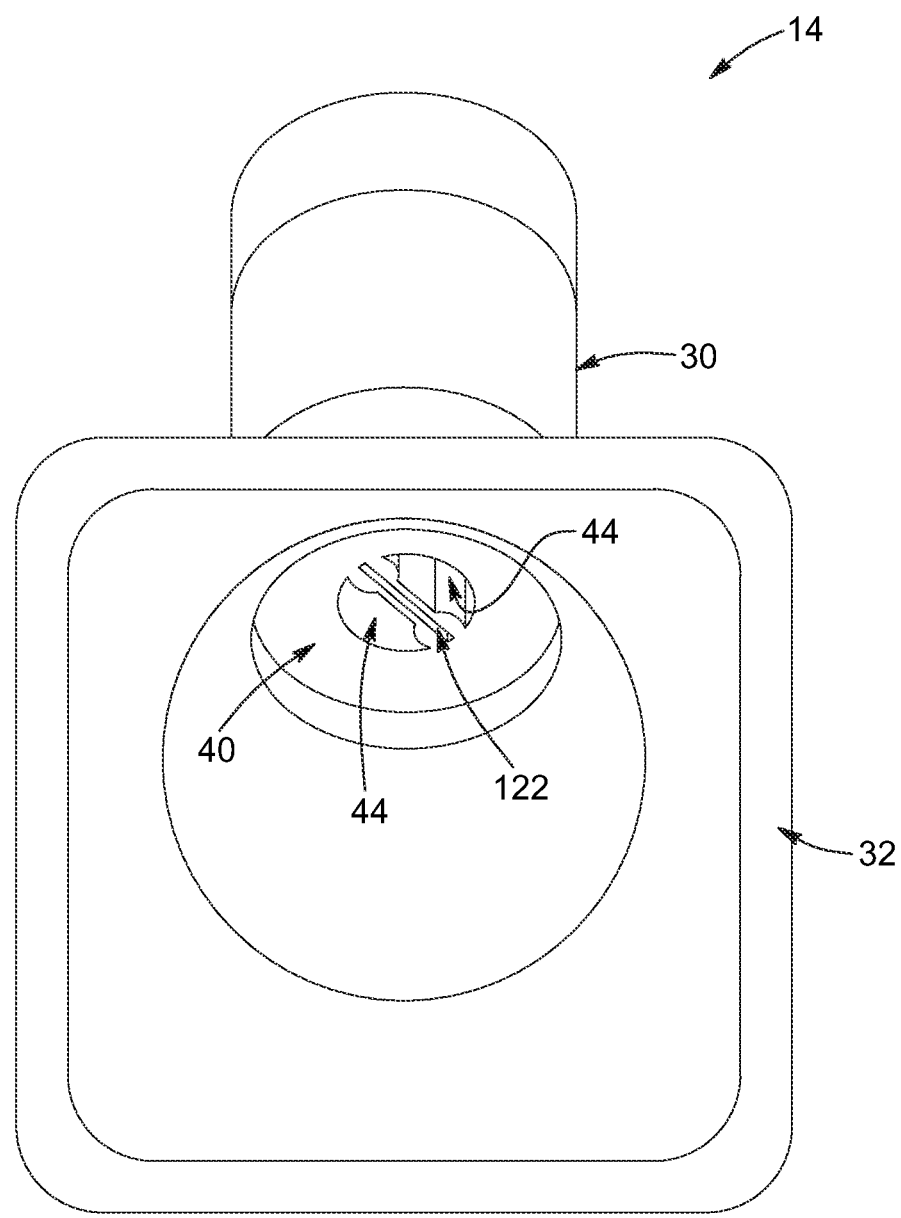
FIG. 24 is a bottom perspective view of the head component.

Referring now to FIGS. 20, 21 and 22, the head component 14 is shown in greater detail and comprises several features as described hereinabove. The head component 14 may have a tapered section 120 in between the tubular trunk 30 and the base portion 32.

More particularly, as shown on FIGS. 21 and 22, the engagement unit 40 has a slot 122 oriented, sized and configured to receive and engage with the tongue of the container body. In one optional embodiment, the slot 122 may have a shape corresponding to the shape of the tongue as shown in FIG. 18. In such a case, the slot 120 as shown in FIGS. 21 and 22 has two cylindrical portions 124, 126 that extend a part of the way along its length (L) and a central flat portion 128. The cylindrical portions 124, 126 receive and engage the ribs of the tongue while the flat portion 128 receives the tab-shaped portion 118 of the tongue. Providing this matching configuration of the tongue and slot enables improved efficiency and performance.

As the container body 12 is mounted into the head component 14, the lips of the front end of the container body 12 pass axially through the axial channel sections 92 until they abut on the bottom surface of the channels. At the same time, the tongue 112 is inserted into the slot 120 (with the ribs housed in the cylindrical portions) of the engagement unit 40. In this position, the head component 14 and the container body 12 are in a fluid containment mode. Preferably, the head and container body are provided with additional coupling means for snapping or otherwise holding them together in this position. The liquid dispensing applicator may be sold in this pre-assembled form.

The channels allow the lips to rotationally slide therein, when the head component is rotated relative to the container body. Preferably, the channels and lips are provided with locking elements, such that once the handle is rotated within the head component the lips are locked in the rotated position.

The liquid dispensing applicator is assembled as appreciated by referring to the Figs. The container body is inserted into the head component such that the slot receives the tongue or the offset projections as the case may be. In addition, the container body and the head component are provided with corresponding coupling elements, preferably an annular ridge and an annular groove, such that when the handle component is inserted into the head component the ridge snaps into the groove and axially locks the two components together. This is to prevent the components from being pulled apart. The ridge and groove are arranged in order to lock the components axially while allowing rotational movement with respect to each other. In operation, when the head and container body components are rotated with respect to each other, a rupture is caused in the container body. The rupture is achieved by deflection shearing in the case of the offset projections and by at least partially rotationally shearing in the case of the tongue which is torn away from the front end to expose apertures which preferably align at the end of rotation with the passages provided in the engagement unit. Liquid is thus released through the apertures, and flows through the passages into the lower cavity of the head component. The fluid flows into the base, which acts as a housing to the sponge. The base has inset region that is preferably spaced away from the absorbent material, which allows the fluid to then flow into that inset region to improve even distribution over the absorbent material. The absorbent material is mounted to the base, preferably around the perimeter using an adhesive. Once the fluid penetrated through the absorbent material it can be dispensed by the absorbent material.

In operation, the user rotates the container body relative to the head component. Consequently, this causes the lips to slide within the channels and the engagement unit to engage and exert forces on the tongue or offset projections, as the case may be, which are fixedly mounted to the rest of the front end of the container body. At a certain point, the proximal portion of the tongue or offset projection, engaged within the slot, is broken by this rotation. Preferably, a snap signifies the user of the completion of the tongue or offset projection break. The breaking of the tongue or offset projection away from the rest of the handle component creates fluid communication allowing the liquid to flow through the passageway and into the absorbent material. To facilitate this liquid flow, the engagement unit is preferably constructed to have passages which directly communicate with the exposed cavity of the container body after rotation.

Preferably, the engagement unit comprises various walls that are designed to define the slot and passages within the handle component. In some embodiments, the slot and passages may extend in a substantially same direction as illustrated.

Figure 25:
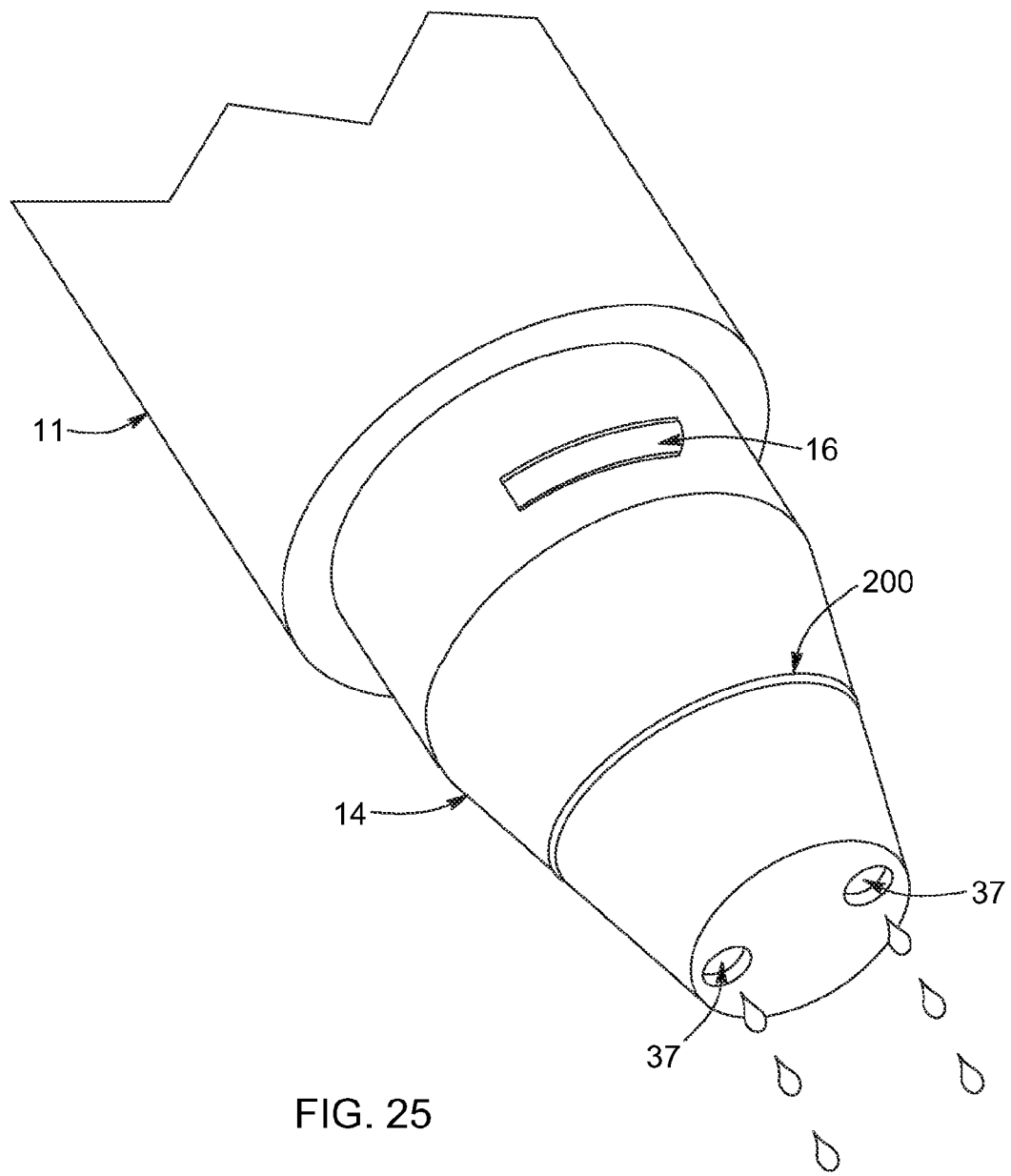
FIG. 25 is a close-up perspective view of the front end of the container body without the tongue member or offset projections.
Figure 26:
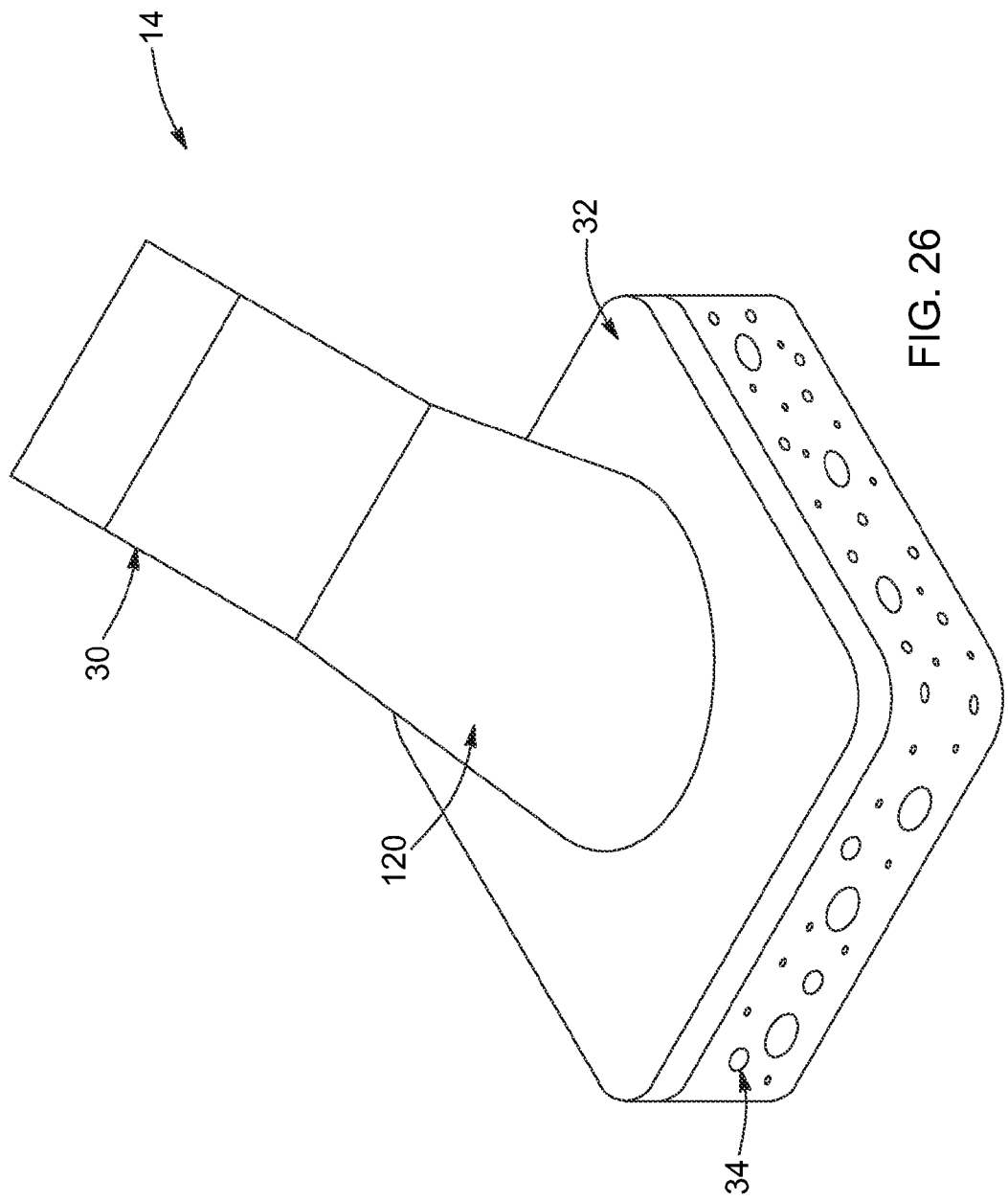
FIG. 26 is a perspective view of the head component coupled with an absorbent material.

As the container body is locked in place with the lips engaged into the channels, a fixed connection is made between the container body and the head component. This connection provides reliability and security for the liquid dispensing applicator during liquid application, the head and handle components being secured together and acting as an integral unit. In addition, by providing a locking mechanism between the head and container body components once rotated to the liquid dispensing position, single-use of the liquid dispensing applicator is facilitated since the head and container body components cannot be detached, refilled or reused. Once rotation has taken place the broken tongue or offset projections may remain within the slot and the two apertures are exposed (see FIG. 25). The passages of the engagement unit are preferably sized and configured in relation to the channels and lips such that after full rotation the exposed apertures are aligned and communicate with the passages, thus ameliorating liquid flow.

The container body is preferably moulded such that the ribs of the tongue cap the apertures, which are then exposed with the breaking of the ribs away from the surrounding region. The ribs or offset projections may be sized as a function of the desired aperture size and engagement with the slot to effect adequate shearing upon rotation. It should also be noted that the tongue and exposable apertures may have a variety of forms and configurations, as long as the breaking of the tongue causes fluid communication between the cavity of the container and the tubular member. In one non-illustrated variant, the cross sections of the passages and the apertures are very similar, e.g. circular, and their alignment enables the fluid communication. It is not imperative that the tongue be completely broken away from the handle component and remain housed within the slot upon rotation; the tongue may be only partially broken away at its lateral ends to expose the apertures while remaining attached at its central portion. It should also be noted that while the preferred method of breaking the tongue is via torsion forces by opposed rotation of the head and container body components along generally longitudinal axes, the head and container body components could also be constructed and arranged such that the tongue and slot engage and are displaced or rotated relative to each other along other axes or vectors to effect the break and enable liquid to be released. The liquid is released from the two apertures into the cavity of the tubular member according to the pressure given by the user by squeezing the container.

The tongue and slot engagement provides a number of advantages for the liquid breaking the tongue. While known applicators depended on subjective deflection applied by a given user to break the tongue, various embodiments of the dispensing applicator of the present invention allow consistent and recognizable breaking by any user, reliable breaking and positioning of the tongue away from the apertures and reliable positioning of the exposed apertures to ensure consistent and proper liquid flow toward the absorbent material. The slot and tongue arrangement is also covered and protected by the surrounding tubular component, which can help improve sterility and hygiene by limiting or eliminating contact with the environment or the user.

The liquid flowing into the cavity of the head component is dispensed through the absorbent material fitted into the base portion. The cavity of the tubular member is in fluid communication with the absorbent material, preferably around the middle of the base portion. This arrangement helps to improve even distribution of the liquid into the absorbent material for improved application. In addition, the angle (about 45°), between the upper surface of the base portion and the tubular member, offers an easy and ergonomic handling of the applicator and efficient squeezing of the container body to allow fluid dispensing. This arrangement provides proper liquid flow through the absorbent material which can be easily maintained in contact with the surface on which the liquid is to be applied.

In another embodiment, as described above, the applicator has "double-lock" functionality. The first lock axially holds the components together and is achieved when the front end of the container body is inserted into the head component. This first locking may be snap action by a groove-ridge engagement. The second lock radially holds the components in a position of fluid release. Upon rotating the components with respect to each other and causing fluid communication between the components, the second lock holds the components in the desired aligned fluid flow position, e.g. with the apertures of the container body aligned with the passages of the head component. It should be understood that many different locking mechanisms or means of achieving the "double-lock" functionality may be used.

In another optional aspect, the container body may be constructed such that the second end is a separate component which has threads for engaging with the main container portion to form the container body. In another aspect, the container body may be constructed such that the second end is glued, adhered, melt bonded, ultrasonically joined or otherwise attached onto the rest of the main container portion. In another aspect, the container body may be constructed as a moulded structure without the offset projections or without the tongue element, as the case may be. The container body may in this case have two openings at the second end and the offset projections or tongue element is then glued, adhered, melt bonded, ultrasonically joined or otherwise attached into place over the openings. In such embodiments, when the container body is rotated in relation to the head component, the offset projections or tongue element may be allowed to break off due to rupture or disconnection of the glue, adhesive, welded region or other attachment means.

In another optional aspect, the liquid dispensing applicator is constructed to provide flow control once the fluid communication has been established. The container body and head component engagement may be so as to establish abutment surfaces to allow a relatively sealed engagement avoiding air re-entry. Surface abutment and alignment of the broken openings and the fluid passageway upon rotation improve the flow control of the applicator.

In another optional aspect, referring to FIGS. 28a-28d, the offset projections 26 may also have support tabs 130 which may have a variety of configurations. There may be support tabs 130 on either side or on a single side of each offset projection. The support tabs may extend above the tip of each offset projection as in FIGS. 28c and 28d, or may end midway up the offset projection as in FIGS. 28a and 28b. The support tabs 130 are preferably configured, sized and given sufficient thickness to provide support to the offset projections 26. Added support can aid during manufacture, packaging, transport and operation of the device to avoid premature or unwanted breakage of the offset projections, for example. It is also preferred, as illustrated, that the support tabs 130 are unitary with the corresponding offset projections 26 and do not span across the rotation axis 24.

In another optional aspect, the liquid is a substance with a viscosity allowing it to flow out of the container body in response to pressure thereon. The liquid may be a substantially Newtonian fluid such as aqueous based fluids for surgical application. The liquid may also be a thicker fluid, semi-liquid fluid, or another fluid for application onto a surface.

In another optional aspect, the invention may also include a one-handed method of applying liquid using a liquid dispensing applicator in which a user, such as a preoperative nurse, grasps the container body of the applicator, twists it relative to the head component causing the projection to break and fluid to be flowable, locks the container body with respect to the head component in the fluid flow position, and then commences application of the liquid onto a surface. All of the steps are easily performable with one hand due to the breaking by rotation and the radial locking mechanism.

The invention claimed is:

1. A liquid dispensing applicator comprising:
   a container body for containing a liquid, the container body having a longitudinal axis about which the container body is rotatable and a first end and a second end, the second end comprising a projection;
   a head component having a passageway having a distal end and a proximal end, the proximal end being for receiving the second end of the container body and the distal end being for applying the liquid onto a surface, the head component comprising a slot system for receiving the projection of the container body;
   wherein the container body and the head component are rotatable with respect to each other to enable engagement of the projection and the slot system and cause breakage of the projection to form a fluid communication breach in the container body, thereby allowing the liquid to flow from the container body into the passageway of the head component; and
   a radial locking system for radially locking the container body and the head component together after rotation with respect to each other.

2. The liquid dispensing applicator of claim 1, wherein the projection is at least one offset projection located so as to avoid traversing the longitudinal axis.

3. The liquid dispensing applicator of claim 2, wherein the offset projection is a first offset projection and the container body comprises at least one additional offset projection, constituting a plurality of offset projections.

4. The liquid dispensing applicator of claim 1, wherein the projection is a tongue arranged so as to rotate in response to rotation of the container body with respect to the head component.

5. The liquid dispensing applicator of claim 1, wherein the radial locking system comprises a lip-and-channel system.

6. The liquid dispensing applicator of claim 5, wherein the lip-and-channel system comprises at least one lip and at least one corresponding channel with a locking nodule over which the lip passes.

7. The liquid dispensing applicator of claim 6, wherein the at least one lip is provided on the container body and the at least one corresponding channel is provided on an inner surface of the head component.

8. The liquid dispensing applicator of claim 7, wherein the at least one lip comprises two opposed lips on either side of the container body and the at least one channel comprises two opposed radial channels.

9. The liquid dispensing applicator of claim 1, wherein the radial locking system is configured such that the container body and the head component are locked together so that the fluid communication breach is aligned with the passageway.

10. The liquid dispensing applicator of claim 1, wherein the radial locking system is configured such that the container body is locked with respect to the head component in a fluid flow position wherein fluid flow apertures of the container body are aligned with openings of the passageway.

11. The liquid dispensing applicator of claim 1, wherein the radial locking system comprises a lip-and-channel system comprising at least one lip and at least one corresponding channel, the lip being radially slidable within the channel, the channel comprising a locking nodule at a far end thereof, wherein rotation from an initial position toward a breakage position causes the lip to slide through the channel and pass over the locking nodule.

12. The liquid dispensing applicator of claim 11, wherein the locking nodule is configured to prevent the lip from sliding back to the initial position.

13. The liquid dispensing applicator of claim 1, wherein the first end of the container body has a pinched part and the radial locking system is configured such that the container body and the head component are locked together so that the pinched part is oriented for easy and ergonomic grasping.

14. The liquid dispensing applicator of claim 1, further comprising an axial coupling system for axially coupling the head component to the container body.

15. The liquid dispensing applicator of claim 1, wherein the container body has a central portion in between the first end and the second end, and the central portion is made of a deformable material so as to be squeezable in order to allow a user to influence pressure exerted on the liquid and control liquid flow.

16. The liquid dispensing applicator of claim 1, wherein the head component further comprises a base portion for supporting an absorbent material; the head component further comprises a downstream cavity in between the passageway and the base portion, for allowing the liquid to flow there-through toward the absorbent material; and the base portion comprises an inset region having a bottom surface, and a lower perimeter surrounding the inset region, the absorbent material being attached to the lower perimeter a leaving a space between the absorbent material and the bottom surface, the space being sized and provided so as to allow the liquid to flow into the inset region.

17. The liquid dispensing applicator of claim 1, wherein the radial locking system comprises:
 a channel;
 a protrusion extendable into the channel for radial displacement therein between a first position and a second position when the head component and the container body are rotated with respect to each other to enable the breakage; and
 a retention element for engaging the protrusion at the second position to resist radial displacement of the protrusion back toward the first position.

18. The liquid dispensing applicator of claim 17, wherein the head component comprises a tubular trunk having an inner surface that includes the channel, and the container body comprises the protrusion extending from an outer surface thereof.

19. The liquid dispensing applicator of claim 17, wherein the channel comprises a radial channel section and an axial channel section that are interconnected so that the protrusion is axially slideable through the axial channel when axially coupling the head component to the container body and then is radially slideable along the radial channel section when the head component and the container body are rotated with respect to each other.

20. The liquid dispensing applicator of claim 17, wherein the retention element comprises a nodule extending from within the channel at a far end thereof.

21. The liquid dispensing applicator of claim 20, wherein the radial displacement of the protrusion between the first position and the second position causes the protrusion to slide through the channel and pass over the nodule, and the nodule is configured to prevent the protrusion from sliding back.

22. The liquid dispensing applicator of claim 17, wherein the retention element is configured as a round bump.

23. The liquid dispensing applicator of claim 17, wherein the retention element is configured as an inclined block with a straight back edge, as a ledge defined by a sloping channel section, or as a flexible tab-like nodule.

24. The liquid dispensing applicator of claim 17, wherein the retention element is provided so at to extend from a bottom surface of the channel.

25. The liquid dispensing applicator of claim 1, wherein the radial locking system comprises:
 an elongated slot provided through a tubular trunk of the head component;
 a rod extending from the container body so as to pass through the elongate slot and be slidable therein; and
 a retention element at a far end of the elongated slot to resist back sliding of the rod after rotation.

26. The liquid dispensing applicator of claim 1, wherein the container body is formed as a one-piece structure made from a plastic material.

27. The liquid dispensing applicator of claim 1, wherein the container body is assembled from two or more parts that are fused, melted or screwed together.

* * * * *